US007771978B2

(12) United States Patent
Clausen et al.

(10) Patent No.: US 7,771,978 B2
(45) Date of Patent: Aug. 10, 2010

(54) β1,4MANNOSYLTRANSFERASES

(75) Inventors: Henrik Clausen, Søbrinken 6, 2840 Holte (DK); Hans Heugh Wandall, Sølvgade 20, st. tv., 1307 Copenhagen K (DK)

(73) Assignees: Henrik Clausen, Holte (DK); Hans Heugh Wandall, Copenhagen (DK)

( * ) Notice: Subject to any disclaimer, the term of this patent is extended or adjusted under 35 U.S.C. 154(b) by 321 days.

(21) Appl. No.: 10/947,638

(22) Filed: Sep. 22, 2004

(65) Prior Publication Data

US 2005/0148047 A1 Jul. 7, 2005

Related U.S. Application Data

(60) Provisional application No. 60/504,920, filed on Sep. 22, 2003.

(51) Int. Cl.
*C12N 9/00* (2006.01)
*C12N 9/10* (2006.01)
*C12N 15/00* (2006.01)
*C07K 14/00* (2006.01)
*C07H 21/04* (2006.01)

(52) U.S. Cl. .................... 435/193; 435/183; 435/320.1; 530/350; 536/23.2

(58) Field of Classification Search ................ 435/183, 435/193, 320.1, 252.3; 530/350; 536/23.2
See application file for complete search history.

(56) References Cited

U.S. PATENT DOCUMENTS

| | | | |
|---|---|---|---|
| 5,891,698 | A | 4/1999 | Prieto et al. |
| 5,955,347 | A | 9/1999 | Lowe |
| 6,046,040 | A | 4/2000 | Nishiguchi et al. |
| 6,204,431 | B1 | 3/2001 | Prieto et al. |
| 6,406,894 | B1 | 6/2002 | Hoersch et al. |
| 6,485,930 | B1 | 11/2002 | Wong |

OTHER PUBLICATIONS

Accession Q03562. Wilson et al. Feb. 1, 1994.*
Accession ABB64561. Venter et al. Mar. 26, 2002.*
Chica et al. Curr Opin Biotechnol. Aug. 2005;16(4):378-84.*
Witkowski et al. Biochemistry. Sep. 7, 1999; 38(36): 11643-50.*
Seffernick et al. J Bacteriol. Apr. 2001; 183 (8): 2405-10.*
Accession Q03562. Feb. 1, 1994.*
Goode, S., et al., The Neurogenic Genes Egghead And Brainiac Define A Novel Signaling Pathway Essential For Epithelial Morphogenesis During Drosophila Oogenesis, Development (1996): 122, p. 3863-3879.
Goode, S., et al., The Neurogenic Locus Brainiac Cooperates With The Drosophila EGF Receptor To Establish The Ovarian Follicle And To Determine Its Dorsal-Ventral Polarity, Development (1992):116, p. 177-192.
Moloney, D. J., et al., Fringe Is A Glycosyltransferase That Modifies Notch, Nature (2000): 406, p. 369-375.
Goode, S., et al. Brainiac Encodes A Novel, Putative Secreted Protein That Cooperates With Grk TGFα In The Genesis Of The Follicular Epithelium, Developmental Biology (1996): 178, p. 35-50.
Rubsam, R., et al., The Egghead Gene Product Influences Oocyte Differentiation by Follicle Cell-Germ Cell Interactions in Drosophila Melanogaster, Mechanisms of Development (1998):72, p. 131-140.
Schwientek, T., et al. The Drosophila Gene Brainiac Encodes A Glycosyltransferase Putatively Involved In Glycosphingolipid Synthesis, Journal of Biological Chemistry (2002): 277, No. 36, p. 32421-32429.
Bennett, Eric Paul, et al., Cloning Of A Human UDP-N-Acetyl-α-D-Galactosamine: Polypeptide N-Acetylgalactosaminyltransferase That Complements Other GalNAc-Transferases In Complete O-Glycosylation Of The MUC1 Tandem Repeat, Journal Of Biological Chemistry (1998): 273, No. 46, p. 30472-30481.
Amado, M., et al., Identification And Characterization Of Large Galactosyltranserase Gene Families: Galactosyltransferases For All Functions, Biochimica et Biophysics Acta (1999):1473, p. 35-53.
Henion, T. R., et al., Defining The Minimal Size Of Catalytically Active Primate α1,3 Galactosyltransferase: Structure-Function Studies On The Recombinant Truncated Enzyme, Glycobiology (1994): 4, No. 2, p. 193-201.
Ju, T., et al., A Unique Molecular Chaperone Cosmc Required For Activity Of The Mammalian Core 1 β3-Galactosyltransferase PNAS (2002):99, No. 26, p. 16613-16618.
Wandall, H. H., et al., Drosophila Egghead Encodes A β1,4-Mannosyltransferase Predicted To Form The Immediate Precursor Glycosphingolipid Substrate For Brainiac, Journal of Biological Chemistry (2003): 278, No. 3, p. 1411-1414.

* cited by examiner

*Primary Examiner*—Christian L Fronda
(74) *Attorney, Agent, or Firm*—Frommer Lawrence & Haug LLP; Thomas J. Kowalski; Deborah L. Lu

(57) ABSTRACT

The unique function of the gene egghead as a GDP-mannose: Glcβ1-Cer β1,4 mannosyltransferase is disclosed. The invention discloses isolated DNA molecules and DNA constructs encoding fragments of egghead and derivatives thereof by way of amino acid deletions, substitutions or insertions exhibiting egghead activity, as well as cloning and expression vectors including such DNA, cells transfected with vectors, and recombinant methods for providing egghead protein. Further, the invention discloses methods of obtaining β1,4-mannosylated glycosphingolipids by use of an enzymatically active egghead protein or by using cells stably transfected with a vector including DNA encoding an enzymatically active egghead protein as an expression system for recombinant production of such glycosphingolipids. Also a method for changing, altering or blocking the glycosphingolipid synthesis of cells by stably or transiently transfection with a vector including DNA encoding enzymatically active egghead protein. Furthermore, a novel method for stimulation of the immune system by cell surface presentation of βMan residues is disclosed.

10 Claims, 11 Drawing Sheets

FIG.1

Drosophila Egghead Seq.

```
1
atgaactccaccacaaagcatctgctgcactgcacactgctcatcactgtgatagttacc
 M  N  S  T  T  K  H  L  L  H  C  T  L  L  I  T  V  I  V  T
61
ttcgaagtattctccggcggtattaagattgacgagaactcgttcacgctcgtggatcct
 F  E  V  F  S  G  G  I  K  I  D  E  N  S  F  T  L  V  D  P
121
tggactgaatacggccaattggccacggttctgctgtacttattgcgctttctcacgctg
 W  T  E  Y  G  Q  L  A  T  V  L  L  Y  L  L  R  F  L  T  L
181
ctcacgctgccccaggtgctgttcaatttctgcggcctggtattctacaatgccttcccc
 L  T  L  P  Q  V  L  F  N  F  C  G  L  V  F  Y  N  A  F  P
241
gagaaggtcgtcctcaagggcagccccctgctggcgcccttcatctgcatccgtgtggtc
 E  K  V  V  L  K  G  S  P  L  L  A  P  F  I  C  I  R  V  V
301
acgcgcggcgacttcccggatttggttaagacgaatgtgctgcgcaacatgaacacctgc
 T  R  G  D  F  P  D  L  V  K  T  N  V  L  R  N  M  N  T  C
361
ctagacacgggactggagaactttctcatcgaagtggtcacggacaaggcggtgaatctg
 L  D  T  G  L  E  N  F  L  I  E  V  V  T  D  K  A  V  N  L
421
tcacagcatcgacgcatccgagagatcgttgtgcccaaggagtacaagacgagaaccggg
 S  Q  H  R  R  I  R  E  I  V  V  P  K  E  Y  K  T  R  T  G
481
gcgttgttcaagtcgcgtgccctgcagtattgcctggaggataatgtgaacgtgctgaac
 A  L  F  K  S  R  A  L  Q  Y  C  L  E  D  N  V  N  V  L  N
541
gacagcgactggatcgtccatctggatgaggagacgctgctcacggagaattcggtgcgt
 D  S  D  W  I  V  H  L  D  E  E  T  L  L  T  E  N  S  V  R
601
ggtatcattaactttgtgctggatggcaagcacccgttcggccagggcctgatcacctat
 G  I  I  N  F  V  L  D  G  K  H  P  F  G  Q  G  L  I  T  Y
661
gccaacgagaacgtggtcaattggctgaccacattggcggacagctttcgggtctccgat
 A  N  E  N  V  V  N  W  L  T  T  L  A  D  S  F  R  V  S  D
721
gatatgggcaagctgcgtctgcagttcaagctcttccacaagccgctcttcagctggaag
 D  M  G  K  L  R  L  Q  F  K  L  F  H  K  P  L  F  S  W  K
781
ggcagttatgtggtcacccaggtgagtgctgagcgttcagtgtcctttgacaacggaatc
 G  S  Y  V  V  T  Q  V  S  A  E  R  S  V  S  F  D  N  G  I
841
gacggttcggtggccgaggattgcttcttcgcgatgcgggcctttagccagggctacacg
 D  G  S  V  A  E  D  C  F  F  A  M  R  A  F  S  Q  G  Y  T
901
ttcaacttcatcgagggcgaaatgtacgagaagtcgccgttcacgctgctggacttcctg
 F  N  F  I  E  G  E  M  Y  E  K  S  P  F  T  L  L  D  F  L
961
cagcagaggaaacgatggctccagggcattctgctggtggtccactccaagatgatcccg
 Q  Q  R  K  R  W  L  Q  G  I  L  L  V  V  H  S  K  M  I  P
1021
tttaagcacaagctcctgctgggcatcagtgtctattcgtgggtcaccatgccgctgtcc
 F  K  H  K  L  L  L  G  I  S  V  Y  S  W  V  T  M  P  L  S
1081
acgtcgaacatcatctttgcggcactgtatcccattcctgcccaaatctggttgacttt
 T  S  N  I  I  F  A  A  L  Y  P  I  P  C  P  N  L  V  D  F
1141
gtgtggccttcatcgcggccattaatatctacatgtacgtctttggcgtaatcaagtcct
 V  C  A  F  I  A  A  I  N  I  Y  M  Y  V  F  G  V  I  K  S
1201
ttttcactgtaccgcttcggtttgttccgattcctggcctgcgtgctgggtgcggtgtgc
 F  S  L  Y  R  F  G  L  F  R  F  L  A  C  V  L  G  A  V  C
1261
acgatacccgtgaatgtggttatcgagaatgtggctgtcatttggggcctggtgggcaag
 T  I  P  V  N  V  V  I  E  N  V  A  V  I  W  G  L  V  G  K
1321
aagcacaagttctatgtggttcagaaggatgtgcgcgtactggagactgtctag
 K  H  K  F  Y  V  V  Q  K  D  V  R  V  L  E  T  V  *
```

FIG. 2

```
EGHDROS    : -MNSTKHLLHCTLLTTVIVTFEVFSGGIKIDENSFTLVDPWTEYGQLATVLYLLLRFFTHLJLPQVLFNFCGLVFYNAFPEKVMLKGSPLLAPFICTRV :  99
EGHANOPHEL : MLNSTSKHLHCALLFGLLIVFEIFCGGIKVTESARVALDPWEEYCTLLTIMVLYLLLRFLHLFLPQVLFNEFCGLVTYNAFPEKVMKGSPLLAPFICLRI : 100
EGHCELEGAN : -MNCEVKHALHCAVLMAWLVCFAYFCGVFTEPVEGSVPESPVASYGLIWTVCLYLLRFTALLVEPCLCNLGLMFNAFREKVQLKAAPLISPVCFRV :  99

EGHDROS    : VTRGDFPDLVKTNVLRNMNTCLDTGLENFLHEVVTDKAVNLSQHRRHREIVPKEYKTRTGALFKSRALQYCLEDNVNLNDSDWIVHLDEETLLTENSV : 199
EGHANOPHEL : VTRGDYAELVKTNVLRNMNTCLDIGLENFLHEVVTDKPIGLFPKHRRTREIVVDKEYKTKTGAMFKARALQYCLEDTVNLNNNDWVHLDEETLLTENSV : 200
EGHCELEGAN : VTKGNFPLLVKENIDTNMKTCFEAGMENFIFEVVTDKALNLPPNPRMREVVPTVYKTKSGAKFKARALQYCLEDDVNILQPTDWIVHLDEETLLTNAI : 199

EGHDROS    : RGIINFVLIDGKHPFGQGLLITYANENVNWLTTLADSFRVSDDMGKLRLQFKLFHKPEFSWKGSYVVTQVSAERSVSFDNGIDGSVAEDCFFAMRAFSQGY : 299
EGHANOPHEL : RGIINFVLDGKHPFGQGLLITYANENVNWLTTLADSFRVSDDMGKLRLQFKMFHKPYFSWKGSYVVTQVHAEKAVSFDNGIDGSVAEDCFFAMRAFAQGY : 300
EGHCELEGAN : CGILNFCEDGKHQFGQGVITYANGDIVNWLTTLSDSFRVADDMGKLRFQFKLFHKPLFGWKGSYVVTQEAERDVSYDHGMEGSIAEDCFFSMVAMKHGY : 299

EGHDROS    : TFNFIEGEMYEKSPFTLLDFLQQRKRMLQGILLVVHSKMTPFKHLELLGISVWSWVTMPLSTSNIIFAALYPIPCPNLVDFVCAFIAAINYMYVFGVIK : 399
EGHANOPHEL : TFNFIEGEMYEKSPFTLIDFLQQRKRMLQGILLVVWRSTEIPLRNKVLLGISLCSWMIFMPLSTSNMIFAALYPIPCRNLIDFVCAFIAGFNYMYVFGVIK : 400
EGHCELEGAN : SFDFIEGEMHEKSPFTIWDFLQQRKRWLQGILLITVHSSKIAVVHKALALSIYAWATMPLTSLQVFLCPLFPLPRCLPFDFLSFVGALNLYMYIFGVVK : 399

EGHDROS    : SFS-LYRFGLERFLACVLGAVCTIPVNVVIENVAVIWGLVGKKHKFYVVQKDVRVLETV : 457
EGHANOPHEL : SFS-LYRFGLMKFLACVLGALCTIPINVVIENVAVIWGLVGKKNKFYVVQKDVRALVTV : 458
EGHCELEGAN : SFSHKYRNSLLRLAMYLAGALMIIPFNILIENAAVLVGMFGRKDQFYIVNKDIQTV--- : 455
```

Fig. 6  Manβ1→4Glcβ1→1nOctyl (P) + Glcβ1→1nOctyl (S)

Fig.7.
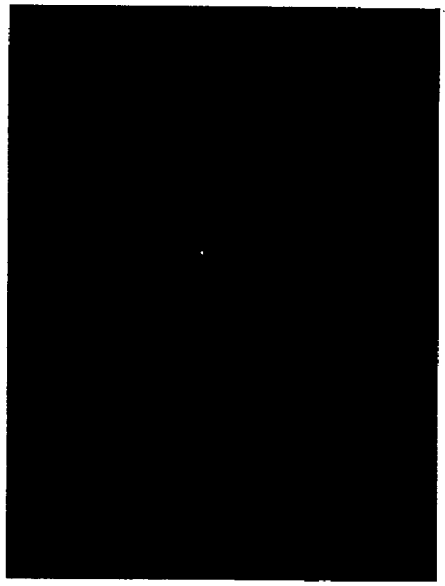

FIGURE 10

KIDENSFTLVDPWTEYGQLATVLLYLLRFLTLLTLPQVLFNFCGLVFYNAFPEKVVLKGSPLLAPFICIRVVTRGDFPDL
VKTNVLRNMNTCLDTGLENFLIEVVTDKAVNLSQHRRIREIVVPKEYKTRTGALFKSRALQYCLEDNVNVLNDSDWIVHL
DEETLLTENSVRGIINFVLDGKHPFGQGLITYANENVVNWLTTLADSFRVSDDMGKLRLQFKLFHKPLFSWKGSYVVTQV
SAERSVSFDNGIDGSVAEDCFFAMRAFSQGYTFNFIEGEMYEKSPFTLLDFLQQRKRWLQGILLVVHSKMIPFKHKLLLG
ISVYSWVTMPLSTSNIIFAALYPIPCPNLVDFVCAFIAAINIYMYVFGVIKSFSLYRFGLFRFLACVLGAVCTIPVNVVI
ENVAVIWGLVGKKHKFYVVQKDVRVLETV

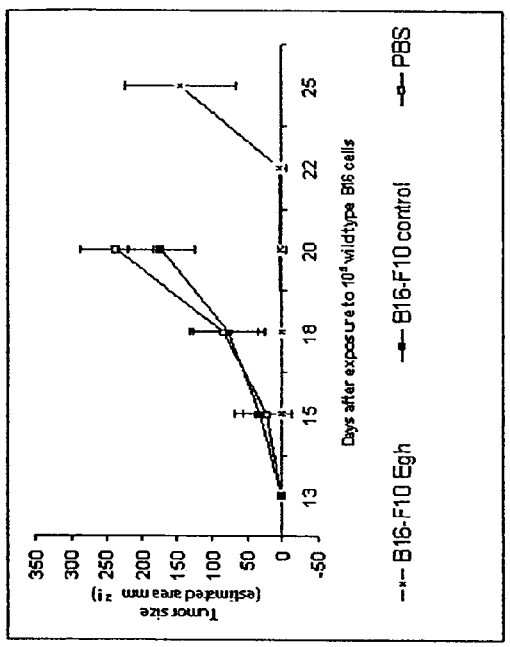
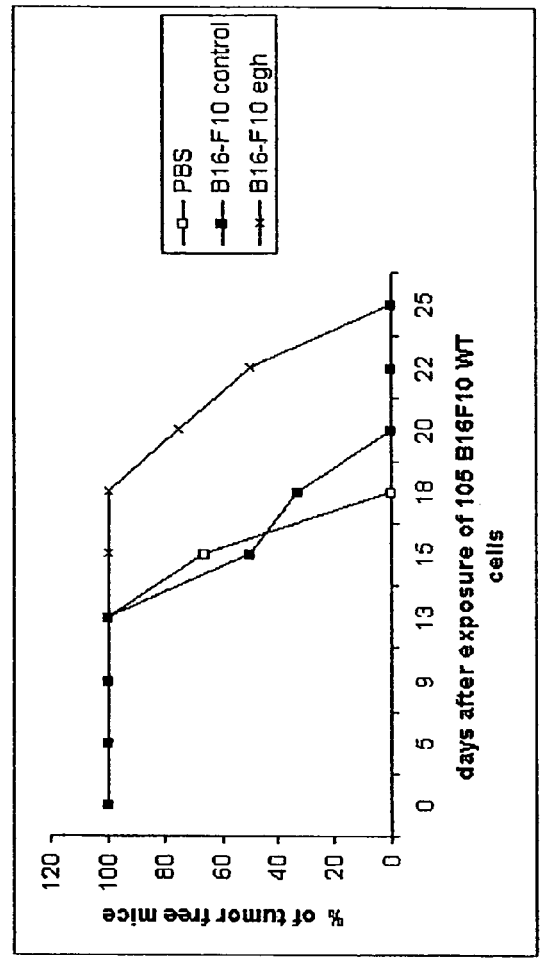
Fig. 11

β1,4 MANNOSYLTRANSFERASES

REFERENCE TO RELATED APPLICATIONS

This application claims priority to U.S. Provisional Application Ser. No. 60/504,920 filed Sep. 22, 2003. This application, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF THE INVENTION

The present invention relates generally to the biosynthesis of glycans found as free oligosaccharides or covalently bound to proteins and glycosphingolipids. This invention is more particularly related polypeptides having glycosyltransferase activity wherein these polypeptides preferably adds mannose to a receiving glycoconjugate. The invention furthermore relates to recombinant methods for stably transfecting cells for expression of the glycosyltranferase of the present invention, methods for changing glycosphingolipid biosynthesis in cells by transfection with the glycosyltranferase of the present invention, and methods for obtaining β-mannose exposure on the surface of mammalian cells leading to immune recognition.

BACKGROUND OF THE INVENTION

The *Drosophila* genes brainiac and egghead have been shown to play essential roles in epithelial development in the embryo and during oogenesis (1-3). Brainiac and egghead encode proteins that are required in the germline to allow for normal interaction between germ-line and somatic cells in the developing ovary (1). In the absence of brainiac or egghead in the germ-line, defects are observed in the overlying follicular epithelium, which is of somatic origin (1;2). On one hand, these follicular epithelial defects resemble defects in EGF receptor signalling between germ-line and follicle cell layers. On the other hand, they resemble a subset of the follicular defects associated with Notch mutants (1;2;4). Defects in female fertility have also been described (5). The diversity of defects caused by brainiac and egghead mutants suggests that they may be involved in communication between cells at a fundamental level and that they can affect multiple signal pathways.

Brainiac and egghead mutants exhibit similar and non-additive phenotypes, leading to the proposal that they function in a common signaling pathway. Signalling pathways are very complex and it may not be possible to predict function of individual genes in such pathways based on genetic studies. For example in a related field, multiple genes were identified based on a common phenotype (Invagination screen) and these genes were later shown to represent many different classes of enzyme activities in different biosynthetic pathways, but all resulting in lack of a particular type of glycoconjugate that preferably was responsible for the phenotype (Hwang H Y, Olson S K, Esko J D, Horvitz H R, Nature. May 22, 2003; 423(6938):439-43).

Based on sequence analysis, Yuan et al. (6) originally proposed that brainiac together with the distant homologous genefringe encoded glycosyltransferases. This hypothesis has subsequently proved correct and both brainiac and fringe represent glycosyltransferases with functionally conserved mammalian homologs (7). Brainiac encodes a UDP-N-acetylglucosamine: βMan β1,3-N-acetylglucosaminyltransferase (β3GlcNAc-T) with a predicted function in biosynthesis of arthroseries glycosphingolipids in the *Drosophila*. Brainiac was shown to catalyze addition of the third monosaccharide residue to form the trihexosylceramide glycolipid, GlcNAcβ1-3Manβ1-4Glcβ1-Cer. Arthroseries glycolipids have only been found in invertebrates and differ fundamentally from mammalian glycolipids by having a core disaccharide structure based on Manβ1-4Glcβ1-Cer (MacCer) rather than Galβ1-4Glcβ1-Cer (LacCer). Brainiac was shown to transfer β1-3 linked GlcNAc to both MacCer and LacCer, while mammalian homologs only transfer to LacCer (7).

SUMMARY OF THE INVENTION

Egghead was originally identified as a secreted or transmembrane neurogenic signaling molecule by Goode et al. (1). The gene sequence was originally deposited by etc (GenBank accession number NM_080313).

Egghead is shown in the present invention to represent a glycosyltransferase gene encoding a novel glycosyltransferase. Egghead is shown to alter the glycosphingolipid biosynthesis in stably transfected mammalian cells expressing the enzyme, and lead to the presentation of non-mammalian antigens on the cell surface recognized by the mannose binding lectin of the innate immune system. More specifically, the present invention describes the identification and characterization of the first gene encoding a β4Man-T glycosyltransferase involved the following procedures described below.

Sequence analysis of egghead indicates that it could encode a type II transmembrane glycosyltransferase being a new class of glycosyltransferases which adds mannose to a receiving hydrocarbon or glycoconjugate. Homologous genes appear limited to invertebrates, and no similar genes are found in the mammalian databases. In the present invention we have shown that egghead encodes a unique invertebrate glycosyltransferase activity in the same biosynthetic pathway as brainiac, and present evidence that egghead indeed encodes a β1,4-mannosyltransferase predicted to form the MacCer precursor glycolipid substrate for brainiac.

It is therefore an object of preferred embodiments of the present invention to provide an isolated polypeptide having mannosyltransferase activity which catalyses the transfer of a mannose from a donor molecule to an acceptor molecule, wherein the donor molecule is a GDP-mannose and the acceptor is selected from the group consisting of a carbohydrate, a glycolipid, a glycoprotein, a synthetic glycoconjugate, a glycopeptide, a proteoglycan, a oligosaccharide and a synthetic compound, wherein the linkage between the mannose and the acceptor molecule is a β-linkage, such as an isolated polypeptide having 4-β-D-mannosyltransferase activity, an enzyme which adds mannose to an acceptor group of an hydrocarbon or a glycoconjugate in a eukaryotic cell.

The exact glycosyltransferase activity of egghead polypeptide is a GDP-D-mannose: β-D-glucose-R 4-β-D-mannosyltransferase (β4Man-transferase), which adds mannose to the hydroxy group at carbon 4 of D-glucose (Glc).

The present invention furthermore provide that the glycoshingolipid synthesis can be blocked in mammalian cells by transfection with an expression construct of egghead that ensures appropriate catalytic function in the secretory pathway and in particular in the Golgi apparatus. Additionally, egghead transfection of mammalian cells results in the presentation of non-mammalian antigens on the surface of mammalian cells, which can be recognized by mannose receptors of the immunesystem such as the mannose binding lectin, MBL, which is an important component of the innate immune system.

It is furthermore an object of preferred embodiments of the present invention to provide homologous genes and proteins from other species which have the same function as egghead, namely mannosyltransferase activity which catalyses the transfer of a mannose from a donor molecule to an acceptor molecule, wherein the donor molecule is a GDP-mannose and the acceptor is selected from the group consisting of a carbohydrate, a glycolipid, a glycoprotein, a synthetic glycoconjugate, a glycopeptide, a proteoglycan, a oligosaccharide and a synthetic compound, and where the linkage between the mannose and the acceptor molecule is a β-linkage.

Yet an object of preferred embodiments of the present invention is to provide nucleic acid vectors comprising DNA sequences encoding mannosyltransferase activity which catalyses the transfer of a mannose from a donor molecule to an acceptor molecule, such as β4Man-transferases, including but not limited to those vectors in which the DNA sequence is operable linked to a transcriptional regulatory element, with or without a polyadenylation sequence.

Cells comprising these vectors are also provided, including without limitation transiently and stably expressing cells. Viruses, including bacteriophages, comprising β4Man-T-derived DNA sequences are also provided.

The invention also encompasses methods for producing polypeptides with mannosyltransferase activity which catalyses the transfer of a mannose from a donor molecule to an acceptor molecule, such as β4Man-transferase. Cell-based methods include without limitation those comprising: introducing into a cell an isolated DNA molecule encoding a polypeptide with mannosyltransferase activity which catalyses the transfer of a mannose from a donor molecule to an acceptor molecule, or a DNA construct comprising a DNA sequence encoding a polypeptide with mannosyltransferase activity which catalyses the transfer of a mannose from a donor molecule to an acceptor molecule; growing the cell under conditions suitable for polypeptide expression; and isolating the polypeptide produced by the cell.

A method for generating a cell with de novo stable expression of a polypeptide with mannosyltransferase activity which catalyses the transfer of a mannose from a donor molecule to an acceptor molecule, such as β4Man-transferase comprises: introducing into a cell an isolated DNA molecule encoding the polypeptide or an enzymatically active fragment thereof (such as, for example, a polypeptide comprising amino acids 29-457 of β4Man-transferase as set forth in SEQ ID NO. 1 or polypeptides having the same function), or a DNA construct comprising a DNA sequence encoding a polypeptide with mannosyltransferase activity which catalyses the transfer of a mannose from a donor molecule to an acceptor molecule or an enzymatically active fragment thereof; selecting and growing host cells in an appropriate medium; and identifying stably transfected cells expressing the polypeptide.

The stably transfected cells may be used for the production of a polypeptide with mannosyltransferase activity which catalyses the transfer of a mannose from a donor molecule to an acceptor molecule for use as a catalyst and for recombinant production of glycosphingolipids, peptides or proteins with desired mannosylation. For example, eukaryotic cells, whether normal or diseased cells, having their glycosylation pattern modified by stable (or transiently) transfection as above, or components of such cells, may be used to deliver specific glycoforms of glycosphingolipids, glycopeptides and glycoproteins, such as, for example, as immunogens for vaccination.

Successful transfection of a polypeptide with mannosyltransferase activity which catalyses the transfer of a mannose from a donor molecule to an acceptor molecule, such as β4Man-transferase in cells can be assessed by immunocytology with antibodies to the enzyme protein or incorporated antibody tags (e.g. myc-tag), by immunocytology with lectins or antibodies detecting the carbohydrate product of the enzyme, by analysis of glycosphingolipids by standard procedures detailed elsewhere, or by analysis of relevant β-mannosyltransferase activity by standard procedures described elsewhere.

In yet another aspect, the invention provides isolated β4Man-T polypeptides, including without limitation polypeptides having the sequence set forth in FIG. 1, polypeptides preferably having the sequence of amino acids 29-457, which truncates the entire predicted transmembrane region (amino acid 8-28), as set forth in FIG. 1, and a fusion polypeptide consisting of at least amino acids 29-457 as set forth in FIG. 1 fused in frame to a second sequence, which may be any sequence that is compatible with retention of β4Man-T enzymatic activity in the fusion polypeptide. The egghead polypeptide may be truncated as described above less or further than 29-457 and checked by methods described herein for retained catalytic function. Suitable second sequences include without limitation those comprising an affinity ligand or a reactive group.

A recombinant soluble secreted egghead protein may be obtained by N-terminal truncation and appropriate expression vector, which preferably includes a cleavable signal sequence. Defining the optimal N-terminal truncation site involves assessing the COOH-terminal end of the catalytic unit of the enzyme, and this may be partially predicted by analysis of conservation of sequence motifs among homologous genes from gene families or orthologous genes from other species (9).

Other factors may play a role for obtaining a functionally active truncated enzyme and expression and analysis of multiple constructs with different N-terminal truncation may be required (10). Selection of suitable host cell for recombinant expression may also require presence of a chaperone necessary for correct folding and function of egghead (11). Defining the minimum egghead sequence containing the catalytic unit can be done by expression of successively N-terminal or C-terminal single amino acid truncated egghead constructs in suitable host cells and with suitable vectors. The catalytic domain of most glycosyltransferase are 200-250 amino acids and generally only few residues can be removed in the C-terminus, whereas it is often possible to successfully express significantly N-terminal truncated glycosyltransferases. General procedures for defining the minimum catalytic unit of glycosyltransferases have been described in detail by Henion et al. (10).

These and other aspects of the present invention will become evident upon reference to the following detailed description and drawings.

BRIEF DESCRIPTION OF THE DRAWINGS

FIG. 1 demonstrates the DNA (small letters, corresponding to SEQ ID NO. 3) and amino acid sequence (capital letters, corresponding to SEQ ID NO. 1) of the egghead gene starting from the initiating Methionine.

FIG. 2 demonstrates a multiple sequence alignment (ClustalW, GeneDoc) of multiple sequence analysis of *Drosophila melanogaster* egghead (SEQ ID NO: 1) and predicted homologues in Anopheles Gambiae (SEQ ID NO: 7) and *C. elegans* (SEQ ID NO: 8). Sequence identity is shown in black boxes (all three sequences were identical) and dark gray boxing (two sequences were identical).

FIG. 7 illustrates Golgi-like localization of egghead by immunostaining of CHO-K1 cells transfected with egghead-full-length construct with a C-terminal myc-tag. Immunofluoresence staining was performed using a commercially available mouse monoclonal anti-myc antibody (Invitrogen) and FITCH-conjugated rabbit anti mouse secondary antibody (DAKO, Denmark).

FIG. 10 demonstrates the amino acid sequence of the mannosyltransferase active part of the egghead sequence, corresponding to SEQ ID NO. 2.

FIG. 11 demonstrates that immunization with egghead transfected mouse melanoma B 16-F10 cancer cells induces tumor immune protection. C57Bl/6 mice were immunized subcutaneous with either irradiated pcDNA3-egghead-Myc-full transfected mouse melanoma cancer cells (B16-F10) (x), control transfected B16-F10 (■) or PBS (□). After 14 days the immunized mice were challenged with wild type B16-F10 cells and tumor growth was monitored. Panel A demonstrates that tumor growth in mice immunized with B16-F10-egghead cells had slow progression compared to mice immunized by either B16-F10 control cells or PBS. Panel B demonstrates that 100% of the mice immunized with egghead transfected B 16-F10 cells (x) remained tumor free for 18 days compared to 13 days in mice immunized with either PBS (□) or control transfected B16-F10 cells (■).

DETAILED DESCRIPTION OF THE INVENTION

Figure 3:
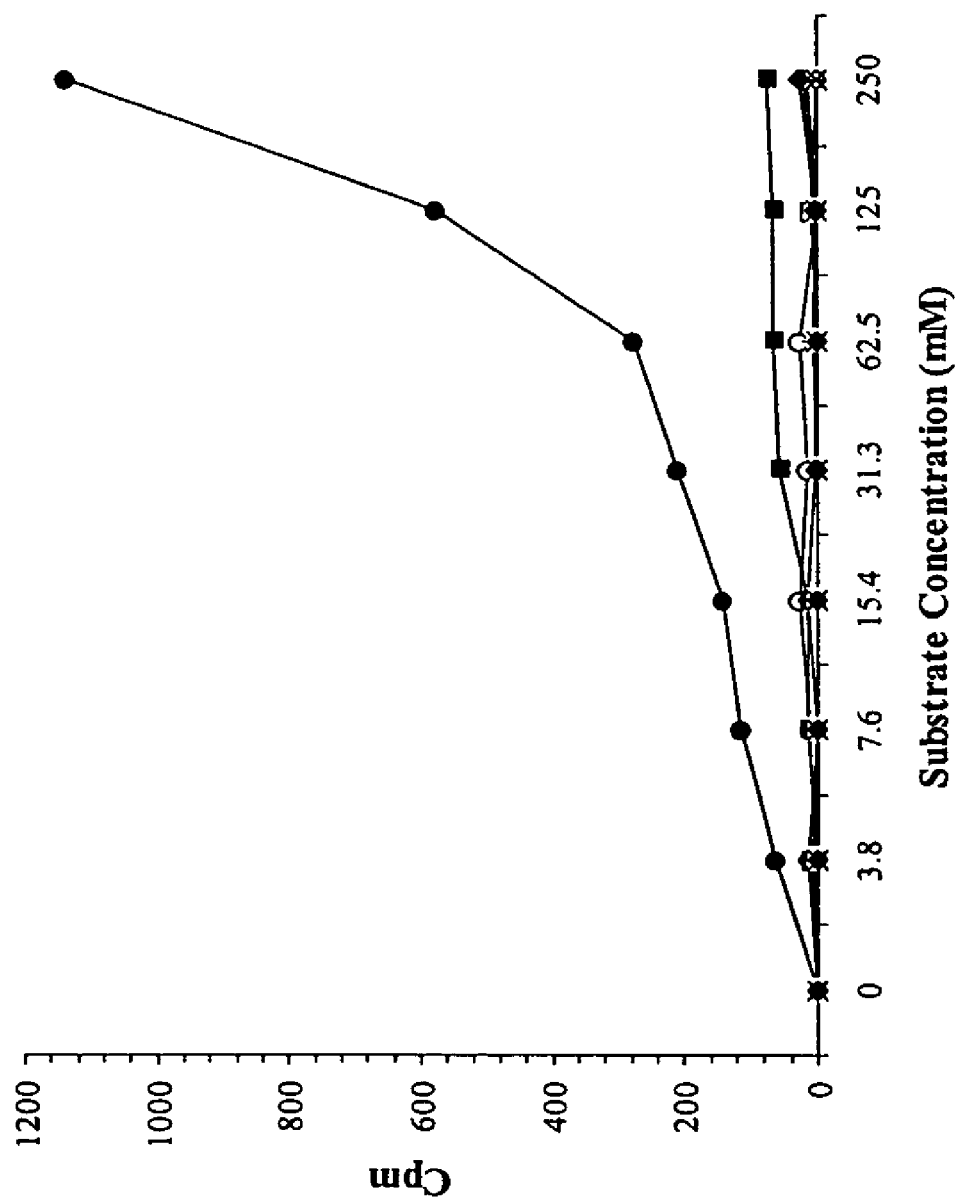
FIG. 3 demonstrates that egghead functions as a glycosyltransferase and exhibits GDP-Man: βGlc mannosyltransferase activity with monosaccharides. Microsomes of transfected High Five™ cells were used as enzyme sources. Donor sugar nucleotides included GDP-Man, UDP-Glc, UDP-Gal, UDP-GlcNAc, UDP-GalNAc, UDP-Xyl. Designations: λ, egghead with GDP-Man and D-Glucose; μ, Control with GDP-Man and D-Glucose; ν, egghead with GDP-Man and L-Mannose; o, Control with GDP-Man and L-Mannose; υ, egghead with GDP-Man and D-Galactose; ◇, Control with GDP-Man and D-Galactose D-Galactose; +, egghead with D-GlcNAc; *, control with D-GlcNAc. Control background values represented activity with microsomal fractions expressing human polypeptide GalNAc-T4.

All patent applications, patents, and literature references cited in this specification are hereby incorporated by reference in their entirety. In the case of conflict, the present description, including definitions, is intended to control.

DEFINITIONS

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in an mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA, which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.).

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of β4Man-T are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. An "orthologous gene" is a homologous gene with significant sequence similarity from another species that encodes an enzyme with the same or similar catalytic function. Significant sequence similarity is a combination of conservation of sequence motifs, cysteine residues and spacing of these in multiple sequence analysis (e.g. Clustal W) (see for details (9)). Most glycosyltransferase genes are highly conserved among close species (mouse-man: approximately 80-98% amino acid sequence conserved; *C. elegans-Drosophila*: approximately 60-80% amino acid sequence conserved; mammalian-insects: approximately 30-60% amino acid sequence conserved). Close orthologs often exhibit conserved sequence motifs throughout the coding region, while homologs family members in a given species often limit conservation to the catalytic unit. While sequence analysis can be used to predict functions of homologous gene products, it is necessary to confirm the prediction with suitable methods such as recombinant expression and characterization of enzyme activity as described herein.

9. Sequence-conservative substitutions or variants refer to nucleic acid changes that conserve the amino acid sequence in the encoded protein due to redundancy in codon usage.

10. Function-conservative substitutions or variants refer to changes in DNA and amino acid sequences that result in enzyme proteins with conserved catalytic function. Determination of function-conservative substitutions will often require expression and characterization of the protein product as described herein to determine functionality.

11. A "donor substrate" is a molecule recognized by, e.g., a mannosyltransferase and that contributes a mannose moiety for the transferase reaction. For β4Man-T, a donor substrate is GDP-mannose. An "acceptor substrate" is a molecule, preferably a saccharide or oligosaccharide, that is recognized by, e.g., a mannosyltransferase and that is the target for the modification catalyzed by the transferase, i.e., receives the mannosyl moiety. For β4Man-T, acceptor substrates include without limitation glycosphingolipids, oligosaccharides, and glycoproteins, containing the terminal monosaccharide βGlc and Glcβ1-ceramide.

12. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity # of identical positions/total # of positions (e.g., overlapping positions)×100). In one embodiment the two sequences are the same length.

Alignment of two sequences for the determination of percent identity is to be accomplished by using a mathematical algorithm published by Tatusova T A, Madden T L (FEMS Microbiol Lett. 1999 May 15; 174(2):247-50). BLAST nucleotide alignments is be performed with the blastn program, with the parameters "Reward for a match"=1, "Penalty for a mismatch"=−2, "Strand option"=both strands, "Open gap"=5, "Extension gap"=2, "gapx_dropoff"=50, "expect"=10.0, "word size"=11 and "Fliter"=on.

BLAST protein searches can be performed with the blastp program applying the "BLOSUM26" matrix, with the parameters "Reward for a match"=1, "Penalty for a mismatch"=−2, "Open gap"=11, "Extension gap"=1, "gapx_dropoff"=50, "expect"=10.0, "word size"=3 and "Fliter"=on.

Both programs can be accessed from National Center for Biotechnological Information's web page at http://www.ncbi.nlm.nih.gov/blast/bl2seq/bl2.html Egghead Encodes a GDP-Man: βGLC β1,4Mannosyltransferase The existence of egghead homologs in Drosophila and other organisms were assessed by tBLASTn searches performed with D. melanogaster egghead coding region (GenBank accession number NM_080313) of the National Center for Biotechnology Information (NCBI) database and the whole genome database GadFly released by the Berkeley Drosophila Genome Project (BDGP). This analysis revealed genes with significant similarity in flies (diptera) and nematodes, including Anopheles gambiae gi|3129832|ref|XP_316840.1|, Anopheles Gambiae str. PEST gi|21299893|gb|EAA12038.1| and C. elegans gi|29603327|emb|CAA79538.2|. Low sequence similarity was found to the putative cellulose synthetase CelA (GenBank accession number AAC41435) from Agrobacterium tumefaciens as well as other bacterial genes predicted to be glycosyltransferases (GenBank accession number NP_348317 [Clostridium acetobutylicum], NP_531181 [Agrobacterium tumefaciens str. C58]). No significant similarity was found with mammalian genes suggesting that egghead encodes an enzyme not found in mammalian cells. It is clear that as more gene and protein sequence information from different species become available additional egghead homologs will become available. By performing similar analysis as shown in FIG. 2 and described herein such putative egghead homologs with the same or similar function can be identified. As examples, the predicted C. elegans egghead protein is approximately 60% identical to Drosophila egghead in amino acid sequence. The predicted A. Gambiae egghead protein is approximately 80% identical to Drosophila egghead in amino acid sequence.

Egghead is predicted to encode a protein of 457 amino acids with a putative N-terminal signal sequence and a putative hydrophobic transmembrane retention signal (1), which is typical for Golgi located glycosyltransferases. SDS-PAGE western blot analysis with anti-myc antibodies of lysates of baculo-virus infected High Five cells or a stable CHO egghead transfectant revealed a single protein migrating with an apparent molecular weight of 52 Kd (not shown). Subcellular localization of egghead was analyzed by immunofluorescense staining of a stable CHO egghead transfectant, where immunoreactivity was limited to a supranuclear pattern characteristic for Golgi localization (FIG. 7). A similar staining pattern was found for a stable CHO transfectant with human GalNAc-T4 (FIG. 7), as well as transfectants with other human glycosyltransferases. The GadFly database predicts that egghead contains a sugar nucleotide donor substrate-binding site with potential DXD/E binding motifs (16).

Initial assays of activity included a screen with high concentrations of monosaccharide substrates and different donor substrates. Microsomal fractions of infected High Five cells expressing the full coding region of egghead exhibited a marked increase in GDP-Man transferase activity with D-Glucose (FIG. 3). Egghead exhibited strict donor substrate specificity for GDP-Mannose and did not utilize other donor sugar nucleotides tested under similar conditions (UDP-Gal, UDP-GalNAc, UDP-GlcNAc). Analysis of a panel of mono- and disaccharide derivatives showed that egghead exhibits strong preference for substrates containing terminal β-linked glucose (β-Glc) (Table I).

TABLE I

Substrate specificities of Egghead β1-4-mannosyltransferase

| Substrate | Egghead[a] | |
|---|---|---|
| | 1 mM | 5 mM |
| | nmol/h/mg | |
| Glcβ1-MeUmb[c] | 330.0 | 611.4 |
| Glcα1-MeUmb | 1.2 | 12.9 |
| Manβ1-MeUmb | 97 | 171.4 |
| Galβ1-MeUmb | 0.0 | ND[c] |
| GlcNAcβ1-MeUmb | 0.2 | 0.0 |
| Xylβ1-MeUmb | 0.0 | ND |
| Manβ1-4GlcNAc | 0.0 | 0.0 |
| Manα-1-Bzl | 0.0 | ND |
| Glcβ1-pNph | 378.6 | 561.4 |
| Manβ1-pNph | 98.6 | 182.9 |
| GlcNAcβ1-pNph | 0.0 | ND |
| Galβ1-pNph | 0.0 | ND |
| GalNAcβ1-pNph | 0.0 | ND |
| Fucβ1-pNph | 0.0 | 0.0 |
| Galβ1-n-Octyl | 0.0 | 0.0 |
| Glcα1-n-Octyl | 3.6 | 6.5 |
| Glcβ1-n-Octyl | 442.8 | 732.6 |
| Manβ1-4Glcβ1-n-Octyl | 0.0 | 0.0 |

[a]Enzyme sources were microsomal preparations of pVL-Egghead infected High Five ™ cells (see "Experimental Procedures"). Background values obtained with microsomes of cells infected with an irrelevant construct (GalNAc-T4) were subtracted.
[c]Bzl, benzyl; MeUmb, 4-methyl-umbelliferyl; Nph, nitrophenyl; ND, not determined.

Interestingly, some βMan monosaccharide derivatives also served as efficient substrates, however, no activity was found with the disaccharides Manβ1-4GlcNAc and Manβ1-4Glcβ1-n-Oct. Analysis of apparent $K_m$ for the most active substrates identified showed that n-octyl-β-Glc was the preferred acceptor substrate (apparent $K_m$ 0.67±0.08 mM) with Glcβ1-pNph (apparent $K_m$ 1.10±0.3 mM) being comparable and Manβ1-pNph (apparent $K_m$ 2.30±0.5 mM) less preferred. The apparent $K_m$ for GDP-Man with n-octyl-β-Glc acceptor substrate was 58.0±6.2 µM.

Optimization of the enzyme assay using microsomal membranes demonstrated that Triton X-100, Triton CF-54 and Nonidet β-40 inhibited egghead activity at 0.1%, while n-octylgalactoside at 3.4 mM (0.1%) and to a lesser extent CHAPS activated the enzyme. The pH optimum of egghead activity was pH 7-8. Addition of 5 to 10 mM $MgCl_2$ and $MnCl_2$ activated enzyme activity ($Mg^{++}$ being better than $Mn^{++}$) and $CaCl_2$ had no effect, while addition of 10 mM EDTA destroyed the activity.

Analysis of egghead activity in the established CHO transfectant cells showed essentially the same properties as when egghead is expressed in insect cells (not shown).

By simple changes of the reaction conditions, when using other types of donor sugars these sugars may also be useful.

Figure 4:
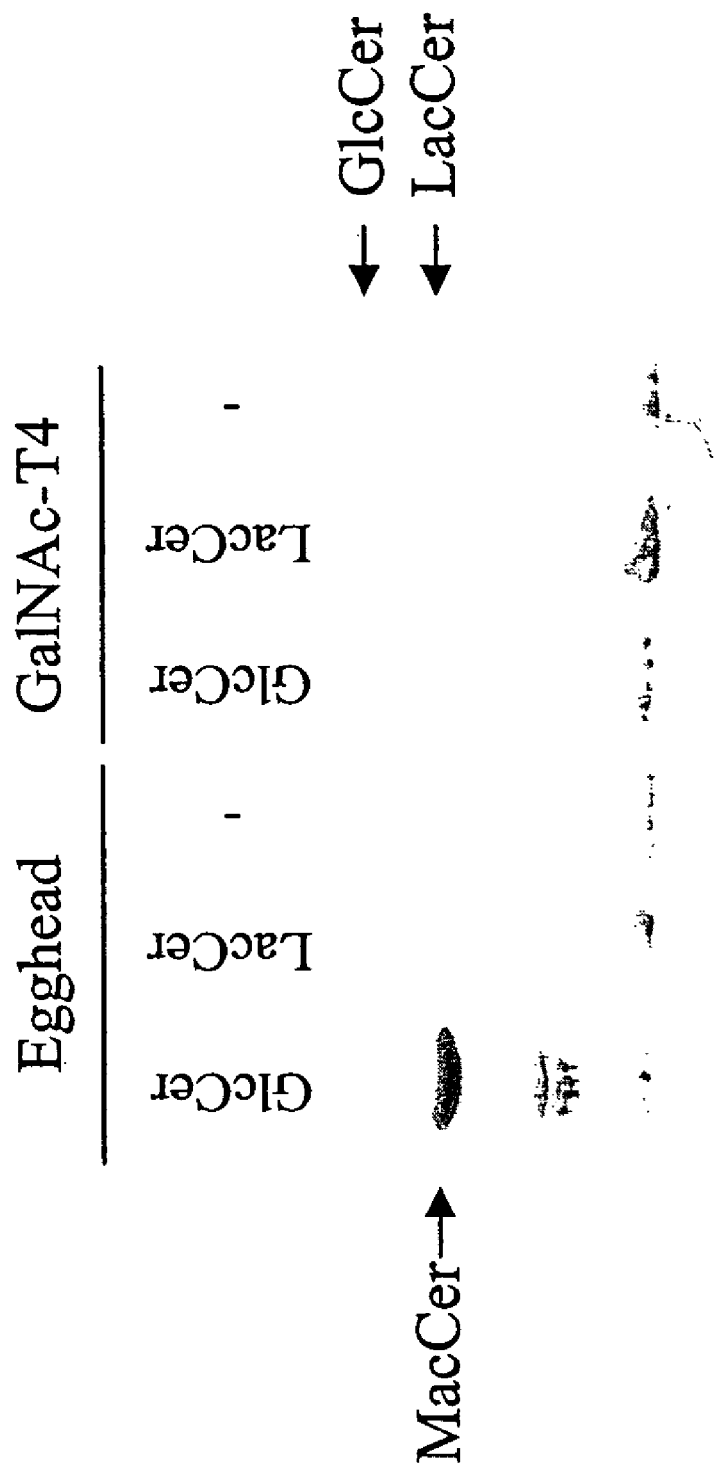
FIG. 4 shows that Egghead transfers Man to Glcβ1-1Cer. Microsomal fraction of egghead (Egh) and GalNAc-T4 (GT4) were incubated with Glcβ1-1Cer, LacCer, or no glycolipid and GDP-Man as described in Experimental Procedures. Autoradiography of thin-layer chromatography of reaction products (4 h). Plate was run in chloroform-methanol-water (60/38/10, v/v/v). Migration of standard glycolipids is indicated with arrows.
Figure 5:
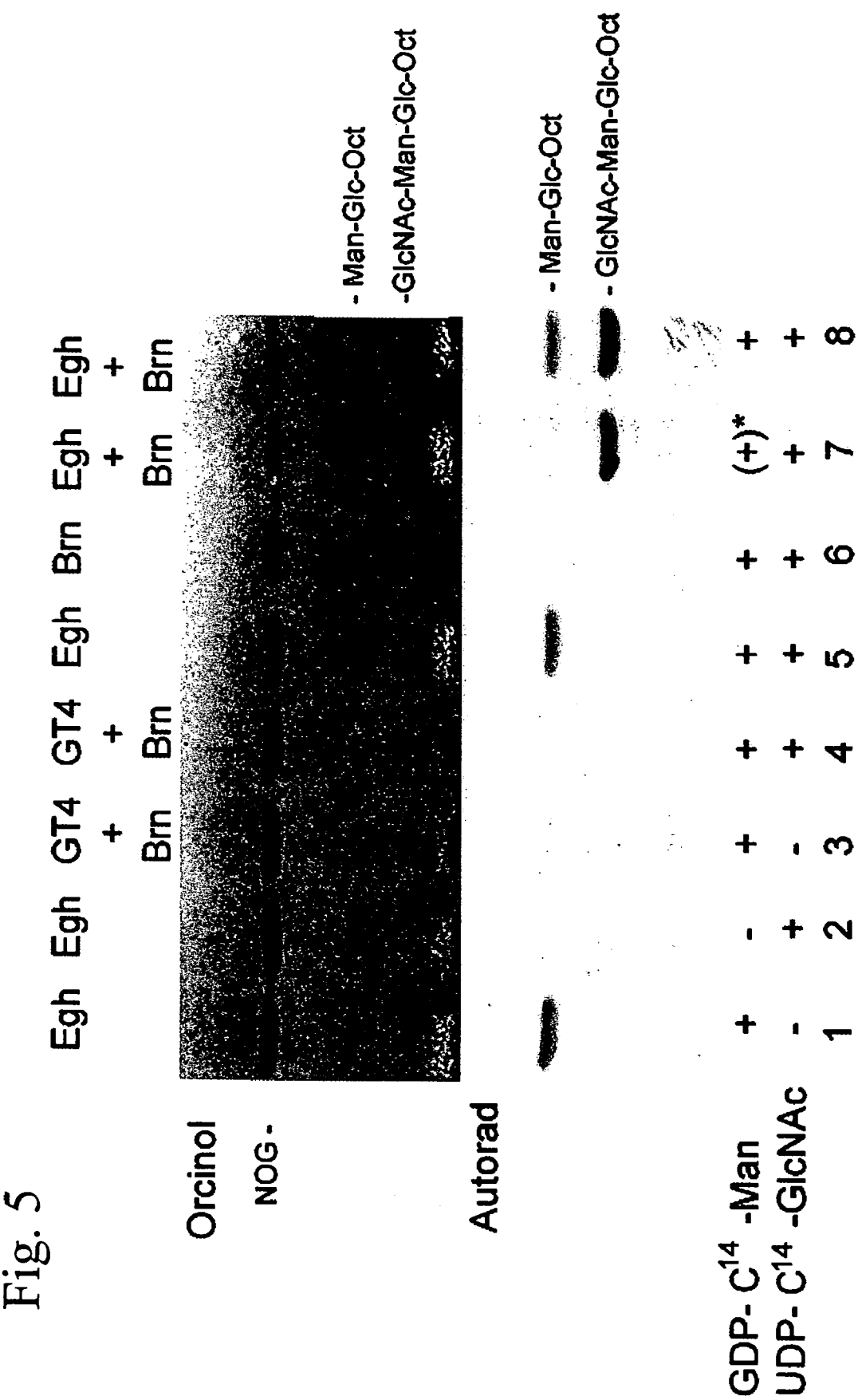
FIG. 5 demonstrates that the product formed by egghead with n-octyl-βGlc serves as a substrate for brainiac. High performance thin layer chromatography analysis of product developments (2 h) with combinations of microsomal fractions of egghead (Egh), polypeptide GalNAc-T4 (GT4), and brainiac (Brn) expressing High Five cells, and combinations of sugar nucleotides GDP-Man and UDP-GlcNAc. Upper panel is stained with orcinol and the lower panel represents an autoradiography. Plates were run in chloroform-methanol-water (60/30/8, v/v/v), and the migration of n-octyl-βGlc (NOG) and the disaccharide and trisaccharide products hereof are indicated in the margins. Man-Glc-Oct is formed only in the presence of egghead and GDP-Man, and GlcNAc-Man-Glc-Oct is formed only in the presence both of egghead and brainiac as well as GDP-Man and UDP-GlcNAc. In lane 7, the asterisks indicate that the autoradiography assay was carried out with non-labeled GDP-Man to confirm that the initial added sugar was Man.

Egghead Functions in Glycosphingolipid Biosynthesis:

Glycosphingolipids of the fruit fly are based on the arthroseries GlcNAcβ1-3Manβ1-4Glcβ1-1 Cer core. The finding that egghead exhibits β-mannosyltransferase activity with βGlc acceptor substrates strongly suggested that egghead transfers Man to Glcβ1-1Cer to form MacCer. As shown in FIG. 4 egghead utilizes Glcβ1-1Cer as an acceptor substrate, whereas LacCer does not serve as substrate. In addition, Galβ1-1Cer was found not to serve as a substrate (not shown). Based on this result it was predicted that egghead functions as the MacCer synthase. Evidence in support hereof was provided by showing that brainiac utilizes the product formed by egghead (FIG. 5). This assay was carried out with n-octyl-β-Glc as initial acceptor substrate because it served as a better substrate than GlcCer under the assay conditions used.

Structural Characterization of Product Formed by Egghead

Figure 6:
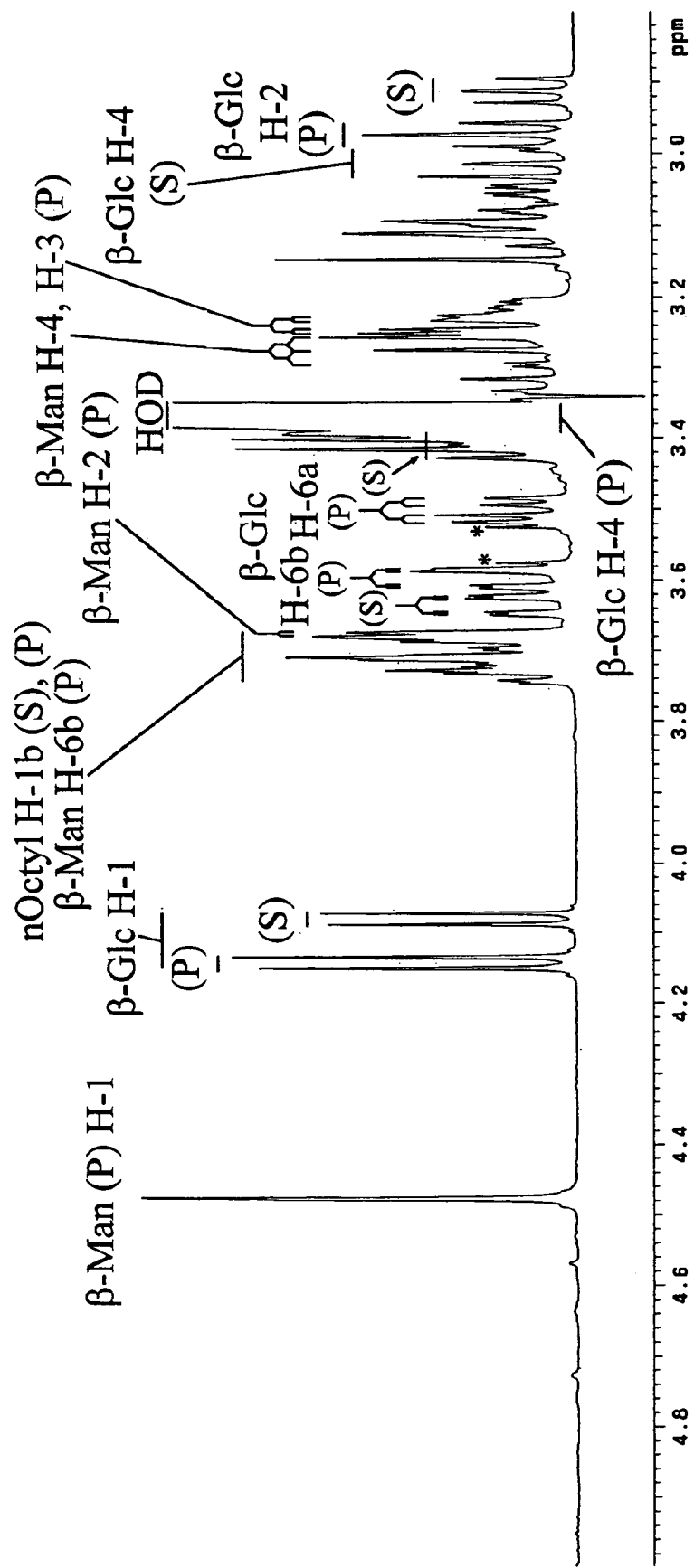
FIG. 6 illustrates the downfield region of 500-MHz $^1$H-NMR spectrum (DMSO-$d_6$/2% $D_2O$, 35° C.) of the Manβ1-4Glcβ1-1nOctyl product of egghead. Arabic numerals refer to ring protons of residues designated by standard three-letter monosaccharide nomenclature in the corresponding structure; P=product; S=substrate. Impurity peaks are marked by asterisks.

A 1-D $^1$H NMR spectrum of the diglycosyl product formed with n-octyl-β-glucoside exhibited resonances consistent with approximately 55% conversion to Manβ1-4Glcβ1-1nOctyl, i.e., anomeric signals at 4.477 and 4.143 ppm ($^3J_{1,2}$=~1 and 7.9 Hz, respectively), corresponding to H-1 of Manβ1-4 and Glcβ1-1 residues of the glycolipid. H-1 of unreacted Glcβ1-1 is observed at 4.080 ppm ($^3J_{1,2}$=7.6 Hz) (FIG. 6). Following complete assignment of $^1$H resonances from all three monosaccharide spin systems present (see Table II) by 2-D $^1$H-$^1$H gCOSY and TOCSY experiments (not shown), the connectivity between the β-Man and the more abundant β-Glc (spin system originating from the H-1 at 4.143 ppm) was established as a 1→4 linkage by a 2-D ROESY experiment; which showed a dipolar cross-relaxation correlation (Overhauser enhancement) between β-Man H-1 and β-Glc H-4. This is consistent with the substantial downfield shift of H-4 compared with that observed for unreacted n-octyl-p-glucoside (3.350 vs 3.016). Although other β-Glc resonances are affected by the glycosylation, H-4 is shifted downfield by the largest increment ($\Delta\delta_{H-4}$=0.334 ppm; $\Delta\delta_{H-3}$=0.244 ppm; $\Delta\delta_{H-5}$=0.151 ppm).

TABLE II $^1$H chemical shifts (ppm) and $^3J_{1,2}$ coupling constants (Hz, in parenthesis) for Glcβ1nOctyl substrate and biosynthetic Manβ4Glcβ1nOctyl product.

| | Manβ4Glcβ1nOctyl[a] | | | Glcβ1nOctyl[a] | |
|---|---|---|---|---|---|
| | Manβ4 | Glcβ1 | nOct | Glcβ1 | nOct |
| H-1 | 4.477 | 4.143 | 3.40, 3.73 (2) | 4.080 | 3.40, 3.71 (2) |
| $^3J_{1,2}$ | (~1) | (7.9) | | (7.6) | |
| H-2 | 3.677 | 2.974 | 1.494 (2) | 2.912 | 1.494 (2) |
| H-3 | 3.239 | 3.316 | ~1.24 (10) | 3.111 | ~1.24 (10) |
| H-4 | 3.275 | 3.344 | | 3.016 | |
| H-5 | 3.094 | 3.215 | | 3.059 | |
| H-6a | 3.395 | 3.500 | | 3.410 | |
| H-6b | 3.695 | 3.597 | | 3.636 | |
| H-8 (CH$_3$) | | | 0.842 (3) | | 0.842 (3) |

[a]Data were obtained in DMSO-d$_6$/2% D$_2$O at 35° C. Chemical shifts are referenced to internal TMS (set to 0.000 ppm).

Figure 9:
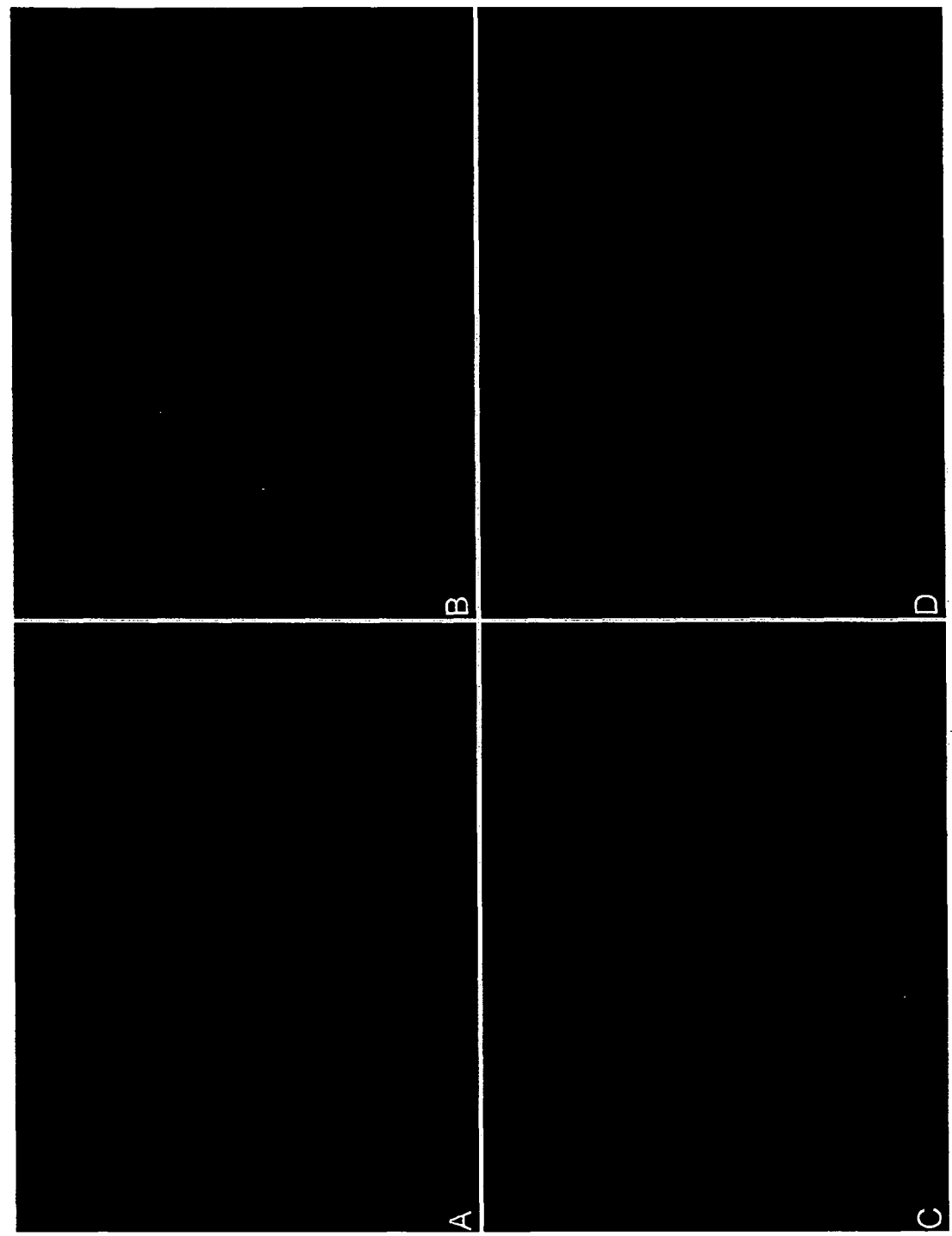
FIG. 9 illustrates binding of human Mannose Binding Lectin to CHO-K1 cells stably transfected with a full coding egghead construct. CHO-K1 cells expressing egghead induced binding of Mannose Binding Lectin to the surface (Panel A). No binding was observed with control cells (Panel B). Furthermore, no labeling was observed in egghead transfected cells (Panel C) and control cells (Panel D) when Mannose Binding Lectin was omitted from the assay, illustrating that the labelling was mediated via the Mannose binding lectin.

CHO-K1 Cells and A431 Cells Expressing Egghead Present Mannose on the Surface that is Strongly Recognized by Human Mannose Binding Lectin, MBL In order to investigate if the expression of egghead in mammalian cells induced recognition by receptors of the human immune system, we evaluated the binding of human Mannose Binding Lectin to egghead-CHO-K1 cells (shown in FIG. 9) and egghead-A431 cell (not shown). Mannose Binding Lectin only bound to CHO cells transfected with egghead (FIG. 9, panel A), but not to control cells (FIG. 9, panel B). No fluorescent labelling was observed in egghead transfected cells (FIG. 9, panel C) and control cells (FIG. 9, panel D) when Mannose Binding Lectin was excluded from the assay conditions, illustrating that the labeling was mediated via the Mannose binding lectin.

DNA, Vectors, and Cells

In practicing the present invention, many conventional techniques in molecular biology, microbiology, recombinant DNA, and immunology, are used. Such techniques are well known and are explained fully in the prior art.

The invention encompasses isolated nucleic acid fragments comprising all or part of the nucleic acid sequence encoding a polypeptide having mannosyltransferase activity which catalyses the transfer of a mannose from a donor molecule to an acceptor molecule, wherein the donor molecule is a GDP-mannose. The fragments are at least about 8 nucleotides in length, preferably at least about 12 nucleotides in length, and most preferably at least about 15-20 nucleotides in length. The invention further encompasses isolated nucleic acids comprising sequences that are hybridizable under stringency conditions of 2×SSC, 55° C., to the sequence set forth in FIG. 1; preferably, the nucleic acids are hybridizable at 2×SSC, 65° C.; and most preferably, are hybridizable at 0.5× SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like. According to the present invention, useful probes comprise a probe sequence at least eight nucleotides in length that consists of all or part of the sequence from among the sequences as set forth in FIG. 1 or sequence-conservative or function-conservative variants thereof, or a complement thereof, and that has been labelled as described above.

The invention also provides nucleic acid vectors comprising the disclosed sequence or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *Saccharomyces cerevisiae, Schizosaccharomyces pombi*, Sf9 cells, C129 cells, 293 cells, *Neurospora*, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced egghead derived peptides and polypeptides.

Figure 8:
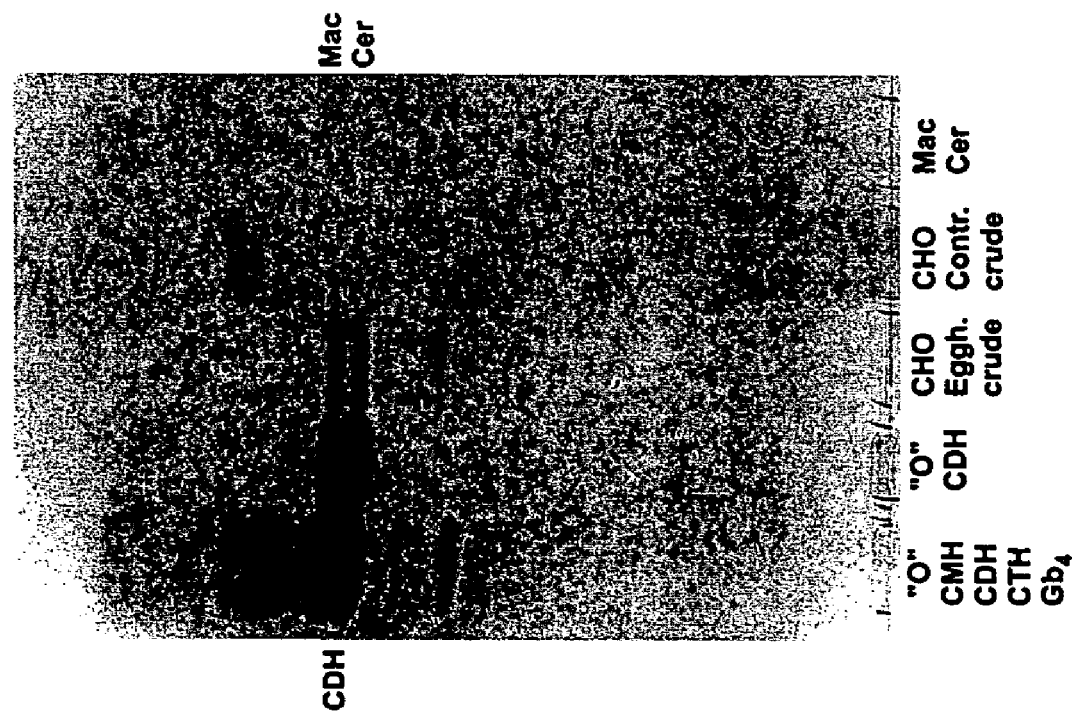
FIG. 8 illustrates a glycosphingolipid analysis of egghead stably transfected CHO-K1 cells and wild type CHO-K1 cells. Glycolipids were analysed by thin-layer chromatography. Plate was run in chloroform-methanol-water (60/38/10, v/v/v). Migration of standard glycolipids is indicated in lane 1. Designations: "O", glycolipids from blood group O erythrocytes; CMH, monohexosyl-ceramide; CDH, dihexosyl-ceramide; CTH, trihexosyl-ceramide; Gb4, globoside; MacCer, mactosylceramide; CHO Contr. crude, total glycolipids prepared from wildtype CHO cells; CHO egghead crude, total glycolipids prepared from stably egghead transfected CHO cells.

Yet another aspect of the present invention is the use of nucleic acids encoding the polypeptide according to the invention having mannosyltransferase activity which catalyses the transfer of a mannose from a donor molecule to an acceptor molecule or a fragment hereof, wherein the donor molecule is a GDP-mannose, such as the egghead gene or sequence-conservative og function-conservative variants thereof or parts of said nucleic acid sequences to transfect mammalian cells with a functional construct or fusion construct, preferably Golgi-located, and achieve β4-mannosylation of endogenous glycoconjugates, including glycolipids as illustrated in FIG. 8. β-Mannose is a potent stimulant of the mammalian immune system and expression of such structures on the surface of autologous or allogeneic cells will lead to broad immune stimulation against cells. The nucleotide sequences encoding the polypeptide of the present invention therefore offer a unique tool to transfect cells to achieve immune stimulation against such cells. This method is of use to stimulate or augment immunity to tumour cells or other normal or diseased cells where it is desirable.

Yet another aspect of the invention is the use of polypeptide of the present invention to block glycolipid elongation in mammalian cells. Blocking glycolipid biosynthesis in normal mammalian cells, diseased cells such as cancer cells, and in particular cells with defects in the breakdown of glycolipids, such as cells from patients with different storage diseases. Gene transfection with the polypeptides of the present invention provides a useful gene therapy.

Advantageously, vectors may also include a transcription regulatory element (i.e., a promoter) operably linked to the egghead coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac Uv5 promoters. Non-limiting examples of yeast promoters include 3-phosphoglycerate kinase promoter, glyceraldehyde-3 phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild-type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as non-homologous recombinations or deletion of endogenous genes by homologous recombination may also be used.

The nucleic acids of the present invention find use, for example, as probes for the detection of or related organisms and as templates for the recombinant production of peptides or polypeptides. These and other embodiments of the present invention are described in more detail below.

Polypeptides of β4MAN-T

The present invention encompasses isolated peptides (generally defined as a polypeptide having less than 50 amino acid residues) and polypeptides encoded by the disclosed genomic sequences. Peptides are preferably at least five residues in length. Peptides and polypeptides may be, for example, 6, 10, 15, 30, 50, 100, 200, or 300 residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of Matteucci et al., 1981, *J. Am. Chem. Soc.* 103:3185, the method of Yoo et al., 1989, *J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well-known in the art, including, without limitation, preparative disc-gel electrophoresis, isoelectric focusing, HPLC, reversed-phase HPLC, gel filtration, ion exchange, affinity chromatography and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

Production of antibodies useful in the present invention can be provided by conventionally used methods well known by the person skilled in the art.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

It is an object of preferred embodiments of the present invention to provide an isolated polypeptide having glycosyltransferase activity, wherein the isolated polypeptide has an amino acid sequence with a sequence identity to SEQ ID NO:1 of less than 100% and more than 20%, such as less than 100% and more than 25%, e.g. less than 100% and more than 30%, e.g. less than 100% and more than 35%, e.g. less than 100% and more than 40%, such as less than 100% and more than 45%, e.g. less than 100% and more than 50%, e.g. less than 100% and more than 55%, such as less than 100% and more than 60%, such as less than 100% and more than 65%, e.g. less than 100% and more than 70%, such as less than 100% and more than 75%, e.g. less than 100% and more than 80%, e.g. less than 100% and more than 85%, such as a sequence identity to SEQ ID NO: 1 of less than 100% and more than 90%.

It is furthermore an object of preferred embodiments of the present invention to provide an isolated polypeptide, wherein the glycosyltransferase activity is mannosyltranferase activity, preferably a βmannosyltransferase such as β1,4manno-syltransferase.

Yet another object of preferred embodiments of the present invention is an isolated polypeptide comprising an amino acid sequence selected from the group consisting of:
a) an amino acid sequence of SEQ ID NO:2; and
b) an amino acid sequence having at least 20% sequence identity to the sequence of SEQ ID NO:2.

In other words the an object of preferred embodiments of the present invention is either a polypeptide having the amino acid sequence of SEQ ID NO:2 or an amino acid sequence having at least 20% sequence identity to the sequence of SEQ ID NO:2, such as at least 25% sequence identity, e.g. at least 30% sequence identity, e.g. at least 35% sequence identity, such as at least 40% sequence identity, e.g. at least 45% sequence identity, e.g. at least 50% sequence identity, such as at least 55% sequence identity, such as at least 60% sequence identity, e.g. at least 65% sequence identity, e.g. at least 70% sequence identity, e.g. at least 75% sequence identity, such as at least 80% sequence identity, e.g. at least 85% sequence identity, e.g. at least 90% sequence identity, such as at least 95% sequence identity, e.g. at least 96% sequence identity, at least 97% sequence identity, at least 98% sequence identity, such as having at least 99% sequence identity to the sequende of SEQ ID NO:2.

In general terms, the isolated polypeptide catalyses the transfer of a mannose from a donor molecule to an acceptor molecule, wherein the donor molecule is a GDP-mannose and the acceptor is selected from the group consisting of a carbohydrate residue, a glycolipid, a glycoprotein, a synthetic glycoconjugate, a glycopeptide, a proteoglycan, a oligosaccharide and a synthetic compound, wherein the linkage between the mannose molecule and the acceptor is a β-linkage.

In an object of preferred embodiments of the present invention the donor and/or the acceptor in the reaction catalysed by the glycosyltransferase of the present invention is modified. The modification of the donor and/or the acceptor is selected from the group consisting of modification by radioisotopes, biotin, and by polyethylene glycol (PEG).

In an object of preferred embodiments of the present invention the isolated polypeptide has GDP-Man: Glcβ1-Cer β1,4-mannosyltransferase activity (β4Man-transferase), an enzymatic activity which adds mannose to the hydroxy group at carbon 4 of D-glucose (Glc).

Thus, a novel class of polypeptides of the present invention can be described as an isolated polypeptides having mannosyltransferase activity which catalyses the transfer of a mannose from a donor molecule to an acceptor molecule, wherein the donor molecule is a GDP-mannose and the acceptor is selected from the group consisting of a carbohydrate, a glycolipid, a glycoprotein, a synthetic glycoconjugate, a glycopeptide, a proteoglycan, a oligosaccharide and a synthetic compound, the linkage between the mannose and the acceptor molecule is a β-linkage, with the proviso that the polypeptide sequence is not identical to SEQ ID NO: 1.

The carbohydrate may be selected from the group consisting of glucose, mannose, galactose and xylose.

Yet another embodiment of the present invention is an isolated nucleotide sequence encoding a polypeptide as described above, with the proviso that the nucleotide sequence is not identical to SEQ ID NO:3, and furthermore, a nucleic acid vector of less than 50,000 nucleotides comprising a first nucleotide sequence identical to or derived from a second nucleotide sequence encoding the polypeptide as described above or a fragment thereof having at least 15 amino acid residues.

Yet another nucleic acid vector of less than 10,000 nucleotides comprising a first nucleotide sequence identical to or derived from a second nucleotide sequence encoding the polypeptide described above or a fragment thereof having at least 120 amino acid residues is an embodiment of the present invention.

The first nucleotide sequence of the vector may be operable linked to a transcriptional regulatory element.

The isolated nucleotide sequence may be DNA, such as cDNA or genomic DNA, or the isolated nucleotide sequence may be RNA.

Yet another object of preferred embodiments of the present invention is a cell comprising the nucleotide sequence according to SEQ ID NO:3 or sequence-conservative variants and function-conservative variants thereof. This nucleotide sequence may be used to stably transfect a cell and thereby providing the glycosyltransferase activity according to the present invention. This glycosyltransferase activity enables the cell to present β-mannose containing glycolipids or β-mannose containing glycoproteins on the cell surface, thereby making said cell immunogenic. The immunogenecity may be caused by the cell being recognized by mannose binding lectins (MBL). MBL is one of many mammalian lectins of the innate immune system, and most of these appear to recognize mannose. Stimulation of the innate immune system provides further stimulation if required of the adaptive immune system leading to B cell and T cell responses. Presentation of βMan residues on glycolipids of mammalian cells is foreign and will strongly stimulate the host immune system.

The cell being transfected with the nucleotide sequence according to the present invention may be selected from the group consisting of mammalian cells, fungi, yeast cells and plant cells. In case of mammalian cells, these cells are selected from the group consisting of mast cells, macrophages, natural killer cells, stem cells, antigen-presenting cells, epithelial cells, dendritic cells, erythrocytes, t-cells, b-cells, plasma cells and any cells derived from one of the listed cells.

A further object of preferred embodiments of the present invention is a method for providing a β-mannose containing glycoconjugate in a media comprising the steps of adding to the media simultaneously or sequentially and in any given order
   1) mannose
   2) a glycoconjugate and
   3) an isolated polypeptide which catalyses the transfer of a mannose from a donor molecule to an acceptor molecule, wherein the donor molecule is a GDP-mannose.

The isolated polypeptide of step 3) may be the polypeptide according to SEQ ID NO:1 or any sequence-conservative variants and function-conservative variants thereof.

The glycoconjugate to which the mannose is added is selected from the group consisting of a carbohydrate, a glycolipid, a glycoprotein, a synthetic glycoconjugate, a glycopeptide, a proteoglycan, a oligosaccharide and any synthetic compound containing a carbohydrate acceptor site. Furthermore, the mannose molecule and/or the glycoconjugate to which the mannose is added may be modified. This modification is selected from the group consisting of modification by radioisotopes, biotin, and polyethylene glycol (PEG).

In a preferred embodiment, the isolated polypeptide provides GDP-Man: Glcβ1-Cer β1,4-mannosyltransferase activity.

A further object of preferred embodiments of the present invention is a method for changing or altering the glycosylation of a compound in a cell comprising the steps of:
   (1) selecting the cell in which the glycosylation of the compound is being changed or altered, and
   (2) transfecting the cell with the nucleotide sequence according to SEQ ID NO:3 or any sequence-conservative variants and function-conservative variants thereof which encodes a polypeptide which catalyses the transfer of a mannose from a donor molecule to an acceptor molecule, wherein the donor molecule is a GDP-mannose.

The cell in which the glycosylation of the compound is being changed or altered is selected from the group consisting of mammalian cells, fungi, yeast cells and plant cells, and the compound is selected from the group consisting of a carbohydrate, a glycolipid, a glycoprotein, a synthetic glycoconjugate, a glycopeptide, a proteoglycan, a oligosaccharide and any synthetic compound containing a carbohydrate acceptor site.

The changing or altering of the glycosylation of the compound in the cell will make the cell capable of presenting immunogenic β-mannose containing glycolipids or β-mannose containing glycoproteins.

A further object of preferred embodiments of the present invention is a method for producing a glycosyltransferase capable of catalysing the synthesis of β-mannose containing glycoconjugates by transferring a mannose from a donor molecule to an acceptor molecule, said method comprising the steps of:
   (i) transfecting the cell with the nucleotide sequence according to SEQ ID NO:3 or any sequence-conservative variants and function-conservative variants thereof which encodes a polypeptide which catalyses the transfer of a mannose from a donor molecule to an acceptor molecule, wherein the donor molecule is a GDP-mannose, and
   (ii) isolating the polypeptide encoded by the nucleotide sequence in step (i) from the media.

The acceptor molecule is selected from the group consisting of a carbohydrate, a glycolipid, a glycoprotein, a synthetic glycoconjugate, a glycopeptide, a proteoglycan, an oligosaccharide, and any synthetic compound containing a carbohydrate acceptor site.

The glycosyltransferase may be able to catalyse the transfer of carbohydrate or derivatives thereof, such as biotin- or polyethylene glycol (PEG) derivatives. The carbohydrates are selected from the group consisting of glucose, mannose, galactose and xylose.

EXAMPLES

Brainiac encodes a UDP-N-acetylglucosamine: βMan β1,3-N-acetylglucosaminyl-transferase (β3GlcNAc-transferase) tentatively assigned a key role in biosynthesis of arthroseries glycosphingolipids and forming the trihexosylceramide, GlcNAcβ1-3Manβ1-4Glcβ1-1Cer (7). In the present invention we demonstrate that egghead encodes a Golgi-located GDP-mannose: βGlc β1,4-mannosyltransferase tentatively assigned a biosynthetic role to form the precursor arthroseries glycosphingolipid substrate for brainiac, Manβ1-4Glcβ1-1Cer (12). Egghead is unique among eukaryotic glycosyltransferase genes in that homologous genes are limited to invertebrates, which correlates with the exclusive existence of arthroseries glycolipids in invertebrates.

Expression of Egghead in Insect Cells

An expression construct of the full coding region of egghead was prepared by RT-PCR using *D. melanogaster* mRNA and the sense primer Egh001 (5'-AGCAGATCTCAAGATGAACTCCACCACAAAG-3', SEQ ID NO: 4) with a BglII restriction site and the anti-sense primer Egh002 (5'-AATAGTCTAGACAGTCTCCAGTACGCG-3', SEQ ID NO: 5) with a XbaI restriction site. The resulting 1.1 Kb fragment was cloned into the BglII/XbaI sites of pVL1393 (PharMingen) and pVL1393-MYC. Furthermore an expression construct for a secreted version of egghead was prepared as described for the full length construct but using sense primer Egh003 (5'AGCAGATCTAAGATTGAC-GAGAACTCGTTC-3', SEQ ID NO: 6) with a BglII restriction site and the anti-sense primer Egh002. The resulting 1 Kb fragment was cloned into pAcGP67 Baculo-virus expression vector. Expression constructs pVL-egghead-full and pVLegghead-Myc-full and pAcGP67-egghead-sol were co-transfected with Baculo-Gold™ DNA (Pharmingen) in Sf9 cells as described (12). Control constructs included pVL-GalNAc-T4-full (8) and pVL-brainiac-full (7). Standard enzyme assays were performed in 50 μl reaction mixtures containing 25 mM HEPES-KOH (pH 7.4), 10 mM $MgCl_2$, 0.1% n-octylgalactoside (Sigma), and 100 μM GDP-[$^{14}$C]-Man (2,000 cpm/nmol) (Amersham), and varying concentration of acceptor substrates (purchased from Fluka, Merck, Sigma and Toronto Research Chemicals Inc; see Table I for structures). Assays with brainiac were carried out in the same reaction mixture except for addition of UDP-[$^{14}$C]GlcNAc (3,000 cpm/nmol) (Amersham) and $MnCl_2$. Enzyme sources were microsomal fractions of baculo-virus infected Sf9 and High Five™ cells prepared essentially as described by Weis et al. (1998). Briefly, cells were lysed in lysis buffer (25 mM Tris-HCl pH 7.4, 250 mM Sucrose), after incubation 30 min on ice cells were homogenized and lysate centrifuged at 1000×G. Glycerol were added to 20% and membrane pellets were obtained by 100.000×g. Pellets were used at 10 mg/ml (Protein concentration determined by BCA, Pierce). Reaction products of soluble acceptors were quantified by chromatography on Dowex AG1-X8 (Sigma). Assays with glycosphingolipids included 5 mM 2-Acetamido-2-deoxy-D-Glucono-1,5-lactone (inhibitor of hexosaminidase activity), and products were purified on octadecyl-silica cartridges (Supelco) and analyzed by high performance thin-layer chromatography followed by autoradiography.

Expression of Egghead in CHO Cells

The 1.1 Kb fragment used for baculo constructs was cloned into the BamH1/Xba1 sites of pcDNA3-zeo(+). CHO-K1 cells were stably transfected with the pcDNA3-egghead-Myc-full, and zeocin resistant clones were selected with anti-Myc antibodies. Cells were grown to subconfluency and fixed with 3% paraformaldehyde and immunostained with anti-Myc monoclonal antibody (Invitrogen). Transferase assays were performed in standard reaction mixtures with cell lysates. CHO-K1 cells stably expressing full coding construct of egghead resulted in strong egghead β4-mannosyltransferase activity with the same properties as when egghead is expressed in insect cells showing that egghead can be functionally expressed in mammalian cell.

Isolation and Analysis of a Product Formed by Egghead

In vitro Glycosylation of n-octyl-glucoside: The product formed with n-octyl-glucoside (1 mg) was purified on octadecyl-silica cartridges (Bakerbond, J. T. Baker), followed by stepwise elution with increasing concentrations of methanol in water. The purified glycolipid was deuterium exchanged by repeated addition of $CDCl_3$-$CD_3OD$ 2:1, sonication, and evaporation under nitrogen, then dissolved in 0.5 mL DMSO-d6/2% $D_2O$ (containing 0.03% tetramethylsilane as chemical shift reference) for NMR analysis. 1-D $^1H$, 2-D $^1H$-$^1H$ gCOSY, TOCSY, and ROESY NMR spectra were acquired on a Varian Inova 500 MHz spectrometer at 35° C., with solvent suppression by pre-saturation pulse, using standard pulse programs included in the Varian vNMR software package.

Glycolipids from CHO-K1 cells transfected with egghead: CHO-K1-Egghead cells were grown and expanded in roller bottles at 37° C. in DMEM with glutamine containing 200 μg/mL zeocin (Invitrogen). The expression of a functional egghead protein was checked of each batch of harvested cells with immuno-histochemstry using anti-myc antibody and by the presence of a β4mannosyltransferase activity.

Approximately 3 ml of packed cells were extracted in 2-propanol-n-hexane-water(55/25/20, v/v/v, upper phase removed) and subjected to Folch partition in chloroform-methanol-water (4/2/1, v/v/v). The dried lower phase glycolipids were freed from other lipids by peracetylation (pyridine-acetic anhydride 2:1 v/v), chromatography on Florisil, and base-catalyzed O-deacetylation and analyzed by HPTLC. The structures of the di-glycosylceramide fractions were determined by $^1H$ NMR spectroscopy and electrospray ionization mass spectrometry to be Manβ1-4Glcβ1-1Cer. Glycosphingolipids were deuterium exchanged by repeated addition of $CDCl_3$-$CD_3O$ D 2:1, sonication, and evaporation under nitrogen, then dissolved in 0.5 ml of $Me_2SO$-$d_6$/2% $D_2O$ (containing 0.03% tetramethylsilane as chemical shift reference) for NMR analysis. A one-dimensional $^1H$ NMR spectrum was acquired on a 600 MHz Varian Inova spectrometer at 35° C., with solvent suppression by presaturation pulse. The identity of glycolipids was established by comparison of the spectrum with those of relevant standards acquired under identical conditions.

CHO-K1 Cells Stably Transfected with Egghead Express Mannose Recognized by Human Mannose Binding Lectin on the Cell Surface In order to investigate if egghead expressing CHO cells are recognized by receptors of the human immune system, we evaluated the binding of human Mannose Binding Lectin to stably egghead transfected CHO-K1 cells. CHO-K1 cells were seeded in 6 well culture dish (NUNC, Denmark). Media was removed and cells washed in binding buffer (Binding buffer, 25 mM Hepes, 155 mM NaCl, 5 mM $CaCl_2$, pH 7,4). After incubating cells with purified human Mannose Binding Lectin (5 μg/ml in binding buffer), cells were washed and detection of bound MBL was evaluated using an anti-MBL mouse monoclonal antibody (Hyb131-10; 1 μg/ml, in binding buffer in 1 hr at RT) followed by detection with a rabbit anti-mouse FITC conjugated polyclonal antibody (DAKO 261, dilution 1:70 in binding buffer in 30 min at RT). Slides (cover slips on culture dish) were mounted in low fade and binding of MBL visualized using a Zeiss Microscope. Mannose Binding Lectin only bound to CHO cells transfected with egghead (FIG. 9, panel A) and not to control cells (FIG. 9. panel B). No fluorescent labeling was observed in egghead transfected cells (FIG. 9. panel C) or control cells (FIG. 9, panel D) when Mannose Binding Lectin was excluded from the assay, demonstrating that the labeling was mediated via the Mannose Binding Lectin.

MBL is one of many mammalian lectins of the innate immune system, and most of these appear to recognize mannose. Stimulation of the innate immune system provides further stimulation if required of the adaptive immune system leading to B cell and T cell responses. Presentation of βMan residues on glycolipids of mammalian cells is foreign and will strongly stimulate the host immune system.

Stable Expression of Golgi-Located Egghead in Human Cancer Cells Changes Glycolipid Biosynthesis The 1.1 Kb fragment used for baculo constructs was cloned into the BamH1/Xba1 sites of pcDNA3-zeo(+). A431 human epidermoid cancer cell line (ATCC CRL-1555) and B16-F10 melanoma cell line (ATCC CRL-6475) cells were stably transfected with the pcDNA3-egghead-Myc-full for transfection of CHO-K1 cells. Golgi-like localization of egghead was determined as described in Example 6.2. Analysis of glycolipids as described in Example can be used to confirm the presence of MacCer, and further corroboration can be achieved with immunostaining with the MBL probe as described in the preceeding Example.

The invention described and claimed herein is not to be limited in scope by the specific embodiments herein disclosed since these embodiments are intended as illustrations only of several aspects of the invention. Any equivalent embodiments are intended to be within the scope of this invention. Indeed, various modifications of the invention in addition to those shown and described herein will be become apparent to those skilled in the art from the foregoing description. Such modifications are also intended to fall within the scope of the appended claims. Throughout this application various references are cited, the contents of each of which ("herein cited documents") is hereby incorporated by reference into the present application in its entirety. Documents cited or referenced in herein cited documents are also hereby incorporated by reference into the present application. Also, manufacturer's specifications, product data sheets and the like for products cited herein, in herein cited documents, and in documents cited or referenced in herein cited documents are hereby incorporated herein by reference. Documents incorporated by reference into this application are not admitted to be prior art; they may be consulted in the practice of the invention, as well as in considering the patentability, e.g., novelty, utility, nonobviousness, of the invention; and, it is noted that the terms "comprising"; "comprised of", "consisting essentially of", "consists essentially of", "consists of" and "consisting of" have the meanings ascribed to these terms in U.S. Patent Law, with it understood that it is an intention of the claims to not read upon or be obvious in view of the prior art.

Cancer Stable Transfected with Golgi-Located Egghead and Expressing Maccer Glycolipids Induce Protective Tumor Immunity.

Mouse melanoma cancer cells (B16-F10, ATCC CRL-6475) were stable transfected with the pcDNA3-egghead-Myc-full vector and as control the empty pcDNA3 vector as described in the preceding example. Stable clones were selected based on anti-Myc and anti-MacCer immunostaining and cloned twice by limited dilution. Mouse anti-MacCer monoclonal antibody was produced in Balb/c by immunization with MacCer glycolipids coated on acid inactivated Salmonella Minnesota bacteria. Stably transfected egghead B 16-F10 cells were irradiated with 75 Gy in order to prevent proliferation and induce apoptosis. C57BL/6 mice were immunized with either egghead transfected cells, control transfected cells or PBS. $1\times10^6$ irradiated egghead B16-F10 cells, $1\times10^6$ control vector cells and PBS were used as immunogen and delivered once by injection subcutaneously in the left flank. After 14 days the immunized mice were challenged with $1\times10^5$ wild type B16-F10 cells by subcutaneous injections in the right flank and tumor growth was monitored by measurement of tumor size with caliper and expressed as measurable area of tumor. As seen in FIG. 11, panel A, tumor growth in mice immunized with B16-F10-egghead cells (x) had slow progression of tumor growth compared to mice immunized by either PBS (□) or B16-F10 control cells (■). Mice were sacrificed when tumors exceeded the ethical acceptable size. FIG. 11, panel B demonstrates that 100% of the mice immunized with egghead transfected B16-F10 cells (x) remained tumor free for 18 days, compared to 13 days in mice immunized with either PBS (□) or control transfected B16-F10 cells (■).

Further Embodiments of the Invention

The invention will now be further described by the following further embodiments:

1. An isolated polypeptide having glycosyltransferase activity, wherein the isolated polypeptide has an amino acid sequence with a sequence identity to SEQ ID NO:1 of less than 100% and more than 20%.

2. An isolated polypeptide according to embodiment 1, wherein the glycosyltransferase activity is mannosyltransferase activity.

3. An isolated polypeptide according to embodiment 2, wherein the mannosyltransferase is capable of providing a β-linkage.

4. An isolated polypeptide according to embodiment 1, wherein the glycosyltransferase activity is β1,4mannosyltranferase activity.

5. An isolated polypeptide comprising an amino acid sequence selected from the group consisting of:
c) an amino acid sequence of SEQ ID NO:2; and
d) an amino acid sequence having at least 20% sequence identity to the sequence of SEQ ID NO:2.

6. The isolated polypeptide according to embodiment 5, wherein the isolated polypeptide has a mannosyltransferase activity.

7. The isolated polypeptide according to embodiment 6, wherein the mannosyltransferase catalyses the transfer of a mannose from a donor molecule to an acceptor molecule, wherein the donor molecule is a GDP-mannose and the acceptor is selected from the group consisting of a carbohydrate residue, a glycolipid, a glycoprotein, a synthetic glycoconjugate, a glycopeptide, a proteoglycan, a oligosaccharide and a synthetic compound, wherein the linkage between the mannose molecule and the acceptor is a β-linkage.

8. The isolated polypeptide according to embodiment 7, wherein the carbohydrate residue is selected from the group consisting of glucose, mannose, galactose, xylose 9. The isolated polypeptide according to embodiment 6, wherein the donor is modified.

10. The isolated polypeptide according to embodiment 6, wherein the acceptor is modified.

11. The isolated polypeptide according to any of paragraphs 9 or 10, wherein the modification of the donor and/or the acceptor is selected from the group consisting of modification by radioisotopes, biotin, and by polyethylene glycol (PEG).

12. The isolated polypeptide according to embodiment 5, wherein the isolated polypeptide having GDP-Man: Glcβ1-Cer β1,4-mannosyltransferase activity.

13. An isolated polypeptide having mannosyltransferase activity which catalyses the transfer of a mannose from a donor molecule to an acceptor molecule, wherein the donor molecule is a GDP-mannose and the acceptor is selected from the group consisting of a carbohydrate, a glycolipid, a glycoprotein, a synthetic glycoconjugate, a glycopeptide, a proteoglycan, a oligosaccharide and a synthetic compound, the linkage between the mannose and the acceptor molecule is a β-linkage, with the proviso that the polypeptide sequence is not identical to SEQ ID NO: 1.

14. The isolated polypeptide according to embodiment 13, wherein carbohydrate is selected from the group consisting of glucose, mannose, galactose and xylose.

15. The isolated polypeptide according to embodiment 13, wherein the donor is modified.

16. The isolated polypeptide according to embodiment 13, wherein the acceptor is modified.

17. The isolated polypeptide according to any of embodiments 15 or 16, wherein the modification of the donor and the acceptor is selected from the group consisting of modification by radioisotopes, biotin, and polyethylene glycol (PEG).

18. The isolated polypeptide according to embodiment 13, wherein the isolated polypeptide has GDP-Man: Glcβ1-Cer β1,4-mannosyltransferase activity.

19. An isolated nucleotide sequence encoding a polypeptide according to any of the preceding embodiments, with the proviso that the nucleotide sequence is not identical to SEQ ID NO:3.

20. A nucleic acid vector of less than 50,000 nucleotides comprising a first nucleotide sequence identical to or derived from a second nucleotide sequence encoding the polypeptide according to any of embodiments 1,5 or 13 or a fragment thereof having at least 15 amino acid residues.

21. A nucleic acid vector of less than 10,000 nucleotides comprising a first nucleotide sequence identical to or derived from a second nucleotide sequence encoding the polypeptide according to any of embodiments 1,5 or 13 or a fragment thereof having at least 120 amino acid residues.

22. The vector of embodiment 21, wherein the first nucleotide sequence is operable linked to a transcriptional regulatory element.

23. A nucleic acid vector of less than 50,000 nucleotides comprising a nucleotide sequence of embodiment 19.

24. An isolated nucleotide sequence according to embodiment 19, wherein the isolated nucleotide sequence is DNA.

25. An isolated nucleotide sequence according to embodiment 24, wherein the DNA is cDNA or genomic DNA.

26. An isolated nucleotide sequence according to embodiment 19, wherein the isolated nucleotide sequence is RNA.

27. A cell comprising the nucleotide sequence of embodiment 19.

28. A cell stably transfected with the nucleic acid vector of any of embodiments 19, 20 or 21.

29. The cell according to embodiments 27 or 28 having the glycosyltransferase activity provided by the polypeptide according to paragraphs 1, 5 or 13.

30. The cell according to embodiment 29, said cell being capable of presenting β-mannose containing glycolipids or β-mannose containing glycoproteins.

31. The cell according to embodiment 30, said cell being immunogenic.

32. The cell according to embodiment 30, said cell recognized by mannose binding lectins 33. The cell according to embodiment 27, wherein the cell is selected from the group consisting of mammalian cells, fungi, yeast cells and plant cells.

34. The cell according to embodiment 33, wherein the mammalian cell is selected from the group consisting of mast cells, macrophages, natural killer cells, stem cells, antigen-presenting cells, epithelial cells, dendrite cells, erythrocytes, t-cells, b-cells, plasma cells and any cells derived from one of the listed cells.

35. A method for providing in a media a β-mannose containing glycoconjugate comprising the steps of adding to the media simultaneously or sequentially and in any given order
  1) mannose
  2) a glycoconjugate and
  3) an isolated polypeptide according to:
    (i) any embodiments 1,5 or 13, or
    (ii) an isolated polypeptide with a sequence identity to SEQ ID NO. 1.

36. The method according to embodiment 35, wherein the glycoconjugate to which the mannose is added is selected from the group consisting of a carbohydrate, a glycolipid, a glycoprotein, a synthetic glycoconjugate, a glycopeptide, a proteoglycan, a oligosaccharide and a synthetic compound.

37. The method according to embodiment 35, wherein the βmannose molecule is modified.

38. The method according to embodiment 35, wherein the glycoconjugate to which the mannose is added is modified.

39. The method according to any of embodiments 37 or 38, wherein the modification of the mannose and the glycoconjugate to which the mannose is added is selected from the group consisting of modification by radioisotopes, biotin, and polyethylene glycol (PEG).

40. The method according to any of embodiment 35, wherein the isolated polypeptide has GDP-Man: Glcβ1-Cer β1,4-mannosyltransferase activity.

41. A method for changing or altering the glycosylation of a compound in a cell comprising the steps of:
  (1) selecting the cell in which the glycosylation of the compound is being changed or altered, and
  (2) transfecting the cell with the nucleotide sequence according to:
    (i) embodiment 19, or
    (ii) SEQ ID NO. 3.

42. The method according to embodiment 41, wherein the cell in which the glycosylation of the compound is being changed or altered is selected from the group consisting of mammalian cells, fungi, yeast cells and plant cells.

43. The method according to embodiment 41, wherein the compound is selected from the group consisting of a carbohydrate, a glycolipid, a glycoprotein, a synthetic glycoconjugate, a glycopeptide, a proteoglycan, a oligosaccharide and any synthetic compound containing a carbohydrate acceptor site.

44. The method according to embodiment 41, wherein the glycosylation of said cell is capable of presenting immunogenic β-mannose containing glycolipids or β-mannose containing glycoproteins.

45. A method for producing a glycosyltransferase capable of catalysing the synthesis of β-mannose containing glycoconjugates by transferring a mannose from a donor molecule to an acceptor molecule, said method comprising the steps of:
  (1) transfecting the cell with a nucleotide sequence according to:
    (i) embodiment 19, or
    (ii) SEQ ID NO. 1, and
  (2) isolating the polypeptide encoded by the nucleotide sequence in step (i) from the media.

46. The method according to embodiment 45, wherein the acceptor molecule is selected from the group consisting of a carbonhydrate, a glycolipid, a glycoprotein, a synthetic glycoconjugate, a glycopeptide, a proteoglycan, an oligosaccharide, and a synthetic compound.

47. The method according to embodiment 45, wherein the enzyme catalysis the transfer of carbohydrate or derivatives thereof.

48. The method according to embodiment 47, wherein the derivative comprises biotin- or polyethylene glycol (PEG) derivatives.

49. The method according to embodiment 48, wherein carbohydrate is selected from the group consisting of glucose, mannose, galactose and xylose.

REFERENCES

1. Goode, S., Melnick, M., Chou, T. B., and Perrimon, N. (1996) *Development* 122, 3863-3879
2. Goode, S., Wright, D., and Mahowald, A. P. (1992) *Development* 116, 177-&
3. Moloney, D. J., Panin, V. M., Johnston, S. H., Chen, J. H., Shao, L., Wilson, R., Wang, Y., Stanley, P., Irvine, K. D., Haltiwanger, R. S., and Vogt, T. F. (2000) *Nature* 406, 369-375
4. Goode, S., Morgan, M., Liang, Y. P., and Mahowald, A. P. (1996) *Developmental Biology* 178, 35-50

5. Rubsam, R., Hollmann, M., Simmerl, E., Lammermann, U., Schafer, M. A., Buning, J., and Schafer, U. (1998) *Mechanisms of Development* 72, 131-140
6.
7. Schwientek, T., Keck, B., Levery, S. B., Jensen, M. A., Pedersen, J. W., Wandall, H. H., Stroud, M., Cohen, S. M., Amado, M., and Clausen, H. (2002) *Journal of Biological Chemistry* 277, 32421-32429
8. Bennett, E. P., Hassan, H., Mandel, U., Mirgorodskaya, E., Roepstorff, P., Burchell, J., Taylor-Papadimitriou, J., Hollingsworth, M. A., Merkx, G., van Kessel, A. G., Eiberg, H., Steffensen, R., and Clausen, H. (1998) *Journal of Biological Chemistry* 273, 30472-30481
9. Amado, M., Almeida, R., Schwientek, T., and Clausen, H. (1999) *Biochimica et Biophysica Acta-General Subjects* 1473, 35-53
10. Henion, T. R., Macher, B. A., Anaraki, F., and Galili, U. (1994) *Glycobiology* 4, 193-201
11. Ju, T. Z. and Cummings, R. D. (2002) *Proceedings of the National Academy of Sciences of the United States of America* 99, 16613-16618
12. Wandall, H. H., Pedersen, J. W., Park, C., Levery, S. B., Pizette, S., Cohen, S. M., Schwientek, T., and Clausen, H. (2003) *Journal of Biological Chemistry* 278, 1411-1414
13. U.S. Pat. No. 6,485,930
14. U.S. Pat. No. 6,406,894
15. U.S. Pat. No. 6,204,431
16. U.S. Pat. No. 6,046,040
17. U.S. Pat. No. 5,955,347
18. U.S. Pat. No. 5,891,698

```
SEQ ID NO: 1 from FIG. 1 (Drosopholia Egghead Seq.)
MNSTTKHLLHCTLLITVIVTFEVFSGGIKIDENSFTLVDPWTEYGQLATVLLYLLRFLTLL

TLPQVLFNFCGLVFYNAFPEKVVLKGSPLLAPFICIRVVTRGDFPDLVKTNVLRNMNTCL

DTGLENFLIEVVTDKAVNLSQHRRIREIVVPKEYKTRTGALFKSRALQYCLEDNVNVLN

DSDWIVHLDEETLLTENSVRGITNFVLDGKHPFGQGLITYANENVVNWLTTLADSFRVSD

DMGKLRLQFKLFHKPLFSWKGSYVVTQVSAERSVSFDNGIDGSVAEDCFFAMRAFSQG

YTFNFIEGEMYEKSPFTLLDFLQQRKRWLQGILLVVHSKMIPFKHKLLLGISVYSWVTMP

LSTSNIIFAALYPIPCPNLVDFVCAFIAAINIYMYVFGVIKSFSLYRFGLFRFLACVLGAVC

TIPVNVVIENVAVIWGLVGKKHKFYVVQKDVRVLETV

SEQ ID NO: 2 from FIG. 10
KIDENSFTLVDPWTEYGQLATVLLYLLRFLTLLTLPQVLFNFCGLVFYNAFPEKVVLKGS

PLLAPFICIRVVTRGDFPDLVKTNVLRNMNTCLDTGLENFLIEVVTDKAVNLSQHRRIREI

VVPKEYKTRTGALFKSRALQYCLEDNVNVLNDSDWIVHLDEETLLTENSVRGIINFVLD

GKHPFGQGLITYANENVVNWLTTLADSFRVSDDMGKLRLQFKLFHKPLFSWKGSYVVT

QVSAERSVSFDNGIDGSVAEDCFFAMRAFSQGYTFNFIEGEMYEKSPFTLLDFLQQRKR

WLQGILLVVHSKMIPFKHKLLLGISVYSWVTMPLSTSNIIFAALYPIPCPNLVDFVCAFIA

AINIYMYVFGVIKSFSLYRFGLFRFLACVLGAVCTIPVNVVIENVAVIWGLVGKKHKFYV

VQKDVRVLETV

SEQ ID NO: 3 from FIG. 1
atgaactccaccacaaagcatctgctgcactgcacactgctcatcactgtgatagttaccttcgaagtattctccggcggtattaagattgacg agaactcgttcacgctcgtggatccttggactgaatacggccaattggccacggttctgctgtacttattgcgctttctcacgctgctcacgctg ccccaggtgctgttcaatttctgcggcctggtattctacaatgccttccccgagaaggtcgtcctcaagggcagcccctgctggcgcccttc atctgcatccgtgtggtcacgcgcggcgacttcccggatttggttaagacgaatgtgctgcgcaacatgaacacctgcctagacacgggact ggagaactttctcatcgaagtggtcacggacaaggcggtgaatctgtcacagcatcgacgcatccgagagatcgttgtgcccaaggagtac aagacgagaaccggggcgttgttcaagtcgcgtgccctgcagtattgcctggaggataatgtgaacgtgctgaacgacagcgactggatc gtccatctggatgaggagacgctgctcacggagaattcggtgcgtggtatcattaactttgtgctggatggcaagcacccgttcggccaggg cctgatcacctatgccaacgagaacgtggtcaattggctgaccacattggcggacagctttcgggtctccgatgatatgggcaagctgcgtc tgcagttcaagctcttcacaagccgctcttcagctggaagggcagttatgtggtcacccaggtgagtgctgagcgttcagtgtcctttgacaa cggaatcgacggttcggtggccgaggattgcttcttcgcgatgcgggcctttagccagggctacacgttcaacttcatcgagggcgaaatgt acgagaagtcgccgttcacgctgctggacttcctgcagcagaggaaacgatggctccagggcattctgctggtggtccactccaagatgat cccgtttaagcacaagctcctgctgggcatcagtgtctattcgtgggtcaccatgccgctgtccacgtcgaacatcatctttgcggcactgtat
```

-continued cccattccctgcccaaatctggttgactttgtgtgcgccttcatcgcggccattaatatctacatgtacgtctttggcgtaatcaagtccttttcact gtaccgcttcggtttgttccgattcctggcctgcgtgctgggtgcggtgtgcacgatacccgtgaatgtggttatcgagaatgtggctgtcattt ggggcctggtgggcaagaagcacaagttctatgtggttcagaaggatgtgcgcgtactggagactgtctag(a)

SEQ ID NO: 4 from text
AGCAGATCTCAAGATGAACTCCACCACAAAG

SEQ ID NO: 5 from text
AATAGTCTAGACAGTCTCCAGTACGCG

SEQ ID NO: 6 from text
AGCAGATCTAAGATTGACGAGAACTCGTTC

SEQ ID NO: 7 from FIG. 2 (EGHANOPHEL)
MLNSTSKHILHCALLFGLLIVFEIFCGGIKVTESAFVAIDPWEEYGTLLTIVLYLLRLLTFL

TLPQVLFNFFGLVIYNAFPEKVVLKGSPLLAPFICIRIVTRGDYAELVKTNVLRNMNTCL

DTGLENFLIEVVTDKPIGLPKHRRTREIVVPKEYKTKTGAMFKARALQYCLEDTVNVLN

NNDWVVHLDEETLLTENSVRGIINFVLDGKHPFGQGLITYANENVVNWLTTLADSFRVS

DDMGKLRLQFKMFHKPYFSWKGSYVVTQVHAEKAVSFDNGIDGSVAEDCFFAMRAFA

QGYTFNFIEGEMYEKSPFTLTDFLQQRKRWLQGILLVVRSTEIPLRNKVLLGISLCSWITM

PLSTSNMIFAAIYPIPCPNLIDFVCAFIAGFNIYMYVFGVIKSFSLYRFGLVKFLACVLGAL

CTIPINVVIENVAVIWGLVGKKNKFYVVQKDVRALVTV

SEQ ID NO: 8 from FIG. 2 (EGHCELEGAN)
MNCEVKHALHCAVLVAWIVCFAYFCGVFTEPVEGSVPESPVASYGLIWTVCLYLLRFTA

LLVLPQCLCNLGGLMMFNAFREKVQLKAAPLLSPFVCFRVVTKGNFPLLVKENIDTNM

KTCFEAGMENFIFEVVTDKAINLPPNPRVREVVVPTVYKTKSGAKFKARALQYCLEDDV

NILQPTDWIVHLDEETLLTTNAICGILNFCEDGKHQFGQGVITYANGDIVNWLTTLSDSF

RVADDMGKLRFQFKLFHKPLFGWKGSYVVTQVEAERDVSYDHGMEGSIAEDCFFSMV

AMKHGYSFDFIEGEMHEKSPFTMWDFLQQRKRWLQGILLTVHSSKIAVVHKALLALSL

YAWATMPLTSLQVFLCPLFPLPRCLPFDFLLSFVGALNLYMYIFGVVKSFSHKYRNSLLR

LAMYLAGALMTIPFNILIENAAVLVGMFGRKDQFYIVNKDIQTV

---

The invention claimed is:

1. An isolated invertebrate polypeptide, wherein the isolated polypeptide has an amino acid sequence with a sequence identity to SEQ ID NO:1 of less than 100% and more than 95% and wherein the isolated polypeptide has GDP-Man: Glcβ1-Cer β-1,4-mannosyltransferase activity.

2. An isolated invertebrate polypeptide, comprising an amino acid sequence selected from the group consisting of:
   a) the amino acid sequence of SEQ ID NO:2;
   b) an amino acid sequence having at least 95% sequence identity to the sequence of SEQ ID NO:2; and,
   wherein the isolated polypeptide has GDP-Man: Glcβ1-Cer β-1,4-mannosyltransferase activity.

3. The isolated polypeptide according to claim 2, wherein the mannosyltransferase catalyses the transfer of a mannose from a donor molecule to an acceptor molecule, wherein the donor molecule is a GDP-mannose and the acceptor is selected from the group consisting of a carbohydrate residue, a glycolipid, a glycoprotein, a synthetic glycoconjugate, a glycopeptide, a proteoglycan, a oligosaccharide and a synthetic compound, wherein the linkage between the mannose molecule and the acceptor is a β-linkage.

4. The isolated polypeptide according to claim 3, wherein the carbohydrate residue is selected from the group consisting of glucose, mannose, galactose, and xylose.

5. The isolated polypeptide according to claim 3, wherein the donor is modified.

6. The isolated polypeptide according to claim 3, wherein the acceptor is modified.

7. The isolated polypeptide according to any of claim 5 or 6, wherein the modification of the donor and/or the acceptor is selected from the group consisting of modification by radioisotopes, biotin, and by polyethylene glycol (PEG).

8. The isolated polypeptide according to claim 2, wherein the isolated polypeptide has GDP-Man: Glcβ1-Cer β1,4-mannosyltransferase activity.

9. An isolated invertebrate polypeptide, wherein the isolated polypeptide has an amino acid sequence with a sequence identity to SEQ ID NO:7 of less than 100% and more than 95% and wherein the isolated polypeptide has GDP-Man: Glcβ1-Cer β-1,4-mannosyltransferase activity.

10. An isolated invertebrate polypeptide, wherein the isolated polypeptide has an amino acid sequence with a sequence identity to SEQ ID NO:8 of less than 100% and more than 95% and wherein the isolated polypeptide has GDP-Man: Glcβ1-Cer β-1,4-mannosyltransferase activity.

* * * * *

SEQUENCE LISTING

<160> NUMBER OF SEQ ID NOS: 8

<210> SEQ ID NO 1
<211> LENGTH: 457
<212> TYPE: PRT
<213> ORGANISM: Drosophila melanogaster

<400> SEQUENCE: 1

Met Asn Ser Thr Thr Lys His Leu Leu His Cys Thr Leu Leu Ile Thr
 1               5                  10                  15

Val Ile Val Thr Phe Glu Val Phe Ser Gly Gly Ile Lys Ile Asp Glu
                20                  25                  30

Asn Ser Phe Thr Leu Val Asp Pro Trp Thr Glu Tyr Gly Gln Leu Ala
            35                  40                  45

Thr Val Leu Leu Tyr Leu Leu Arg Phe Leu Thr Leu Leu Thr Leu Pro
        50                  55                  60

Gln Val Leu Phe Asn Phe Cys Gly Leu Val Phe Tyr Asn Ala Phe Pro
65                  70                  75                  80

```
Glu Lys Val Val Leu Lys Gly Ser Pro Leu Ala Pro Phe Ile Cys
                85                  90                  95

Ile Arg Val Val Thr Arg Gly Asp Phe Pro Asp Leu Val Lys Thr Asn
                100                 105                 110

Val Leu Arg Asn Met Asn Thr Cys Leu Asp Thr Gly Leu Glu Asn Phe
                115                 120                 125

Leu Ile Glu Val Val Thr Asp Lys Ala Val Asn Leu Ser Gln His Arg
            130                 135                 140

Arg Ile Arg Glu Ile Val Val Pro Lys Glu Tyr Lys Thr Arg Thr Gly
145                 150                 155                 160

Ala Leu Phe Lys Ser Arg Ala Leu Gln Tyr Cys Leu Glu Asp Asn Val
                165                 170                 175

Asn Val Leu Asn Asp Ser Asp Trp Ile Val His Leu Asp Glu Glu Thr
                180                 185                 190

Leu Leu Thr Glu Asn Ser Val Arg Gly Ile Ile Asn Phe Val Leu Asp
            195                 200                 205

Gly Lys His Pro Phe Gly Gln Gly Leu Ile Thr Tyr Ala Asn Glu Asn
            210                 215                 220

Val Val Asn Trp Leu Thr Thr Leu Ala Asp Ser Phe Arg Val Ser Asp
225                 230                 235                 240

Asp Met Gly Lys Leu Arg Leu Gln Phe Lys Leu Phe His Lys Pro Leu
                245                 250                 255

Phe Ser Trp Lys Gly Ser Tyr Val Val Thr Gln Val Ser Ala Glu Arg
                260                 265                 270

Ser Val Ser Phe Asp Asn Gly Ile Asp Gly Ser Val Ala Glu Asp Cys
            275                 280                 285

Phe Phe Ala Met Arg Ala Phe Ser Gln Gly Tyr Thr Phe Asn Phe Ile
            290                 295                 300

Glu Gly Glu Met Tyr Glu Lys Ser Pro Phe Thr Leu Leu Asp Phe Leu
305                 310                 315                 320

Gln Gln Arg Lys Arg Trp Leu Gln Gly Ile Leu Val Val His Ser
                325                 330                 335

Lys Met Ile Pro Phe Lys His Lys Leu Leu Leu Gly Ile Ser Val Tyr
                340                 345                 350

Ser Trp Val Thr Met Pro Leu Ser Thr Ser Asn Ile Ile Phe Ala Ala
                355                 360                 365

Leu Tyr Pro Ile Pro Cys Pro Asn Leu Val Asp Phe Val Cys Ala Phe
    370                 375                 380

Ile Ala Ala Ile Asn Ile Tyr Met Tyr Val Phe Gly Val Ile Lys Ser
385                 390                 395                 400

Phe Ser Leu Tyr Arg Phe Gly Leu Phe Arg Phe Leu Ala Cys Val Leu
                405                 410                 415

Gly Ala Val Cys Thr Ile Pro Val Asn Val Ile Glu Asn Val Ala
                420                 425                 430

Val Ile Trp Gly Leu Val Gly Lys His Lys Phe Tyr Val Val Gln
                435                 440                 445

Lys Asp Val Arg Val Leu Glu Thr Val
450                 455

<210> SEQ ID NO 2
<211> LENGTH: 429
<212> TYPE: PRT
<213> ORGANISM: Drosophila melanogaster

<400> SEQUENCE: 2
```

```
Lys Ile Asp Glu Asn Ser Phe Thr Leu Val Asp Pro Trp Thr Glu Tyr
  1               5                  10                  15

Gly Gln Leu Ala Thr Val Leu Leu Tyr Leu Leu Arg Phe Leu Thr Leu
             20                  25                  30

Leu Thr Leu Pro Gln Val Leu Phe Asn Phe Cys Gly Leu Val Phe Tyr
         35                  40                  45

Asn Ala Phe Pro Glu Lys Val Leu Lys Gly Ser Pro Leu Leu Ala
     50                  55                  60

Pro Phe Ile Cys Ile Arg Val Val Thr Arg Gly Asp Phe Pro Asp Leu
 65                  70                  75                  80

Val Lys Thr Asn Val Leu Arg Asn Met Asn Thr Cys Leu Asp Thr Gly
                 85                  90                  95

Leu Glu Asn Phe Leu Ile Glu Val Val Thr Asp Lys Ala Val Asn Leu
             100                 105                 110

Ser Gln His Arg Arg Ile Arg Glu Ile Val Pro Lys Glu Tyr Lys
             115                 120                 125

Thr Arg Thr Gly Ala Leu Phe Lys Ser Arg Ala Leu Gln Tyr Cys Leu
         130                 135                 140

Glu Asp Asn Val Asn Val Leu Asn Asp Ser Asp Trp Ile Val His Leu
145                 150                 155                 160

Asp Glu Glu Thr Leu Leu Thr Glu Asn Ser Val Arg Gly Ile Ile Asn
                 165                 170                 175

Phe Val Leu Asp Gly Lys His Pro Phe Gly Gln Gly Leu Ile Thr Tyr
             180                 185                 190

Ala Asn Glu Asn Val Val Asn Trp Leu Thr Thr Leu Ala Asp Ser Phe
         195                 200                 205

Arg Val Ser Asp Asp Met Gly Lys Leu Arg Leu Gln Phe Lys Leu Phe
         210                 215                 220

His Lys Pro Leu Phe Ser Trp Lys Gly Ser Tyr Val Val Thr Gln Val
225                 230                 235                 240

Ser Ala Glu Arg Ser Val Ser Phe Asp Asn Gly Ile Asp Gly Ser Val
                 245                 250                 255

Ala Glu Asp Cys Phe Phe Ala Met Arg Ala Phe Ser Gln Gly Tyr Thr
             260                 265                 270

Phe Asn Phe Ile Glu Gly Glu Met Tyr Glu Lys Ser Pro Phe Thr Leu
         275                 280                 285

Leu Asp Phe Leu Gln Gln Arg Lys Arg Trp Leu Gln Gly Ile Leu Leu
         290                 295                 300

Val Val His Ser Lys Met Ile Pro Phe Lys His Lys Leu Leu Leu Gly
305                 310                 315                 320

Ile Ser Val Tyr Ser Trp Val Thr Met Pro Leu Ser Thr Ser Asn Ile
                 325                 330                 335

Ile Phe Ala Ala Leu Tyr Pro Ile Pro Cys Pro Asn Leu Val Asp Phe
             340                 345                 350

Val Cys Ala Phe Ile Ala Ala Ile Asn Ile Tyr Met Tyr Val Phe Gly
         355                 360                 365

Val Ile Lys Ser Phe Ser Leu Tyr Arg Phe Gly Leu Phe Arg Phe Leu
         370                 375                 380

Ala Cys Val Leu Gly Ala Val Cys Thr Ile Pro Val Asn Val Val Ile
385                 390                 395                 400

Glu Asn Val Ala Val Ile Trp Gly Leu Val Gly Lys Lys His Lys Phe
                 405                 410                 415
```

```
                Tyr Val Val Gln Lys Asp Val Arg Val Leu Glu Thr Val
                    420                 425

<210> SEQ ID NO 3
<211> LENGTH: 1374
<212> TYPE: DNA
<213> ORGANISM: Drosophila melanogaster
<220> FEATURE:
<221> NAME/KEY: CDS
<222> LOCATION: (1)..(1374)

<400> SEQUENCE: 3 atg aac tcc acc aca aag cat ctg ctg cac tgc aca ctg ctc atc act        48
Met Asn Ser Thr Thr Lys His Leu Leu His Cys Thr Leu Leu Ile Thr
1               5                  10                  15 gtg ata gtt acc ttc gaa gta ttc tcc ggc ggt att aag att gac gag        96
Val Ile Val Thr Phe Glu Val Phe Ser Gly Gly Ile Lys Ile Asp Glu
                20                  25                  30 aac tcg ttc acg ctc gtg gat cct tgg act gaa tac ggc caa ttg gcc       144
Asn Ser Phe Thr Leu Val Asp Pro Trp Thr Glu Tyr Gly Gln Leu Ala
            35                  40                  45 acg gtt ctg ctg tac tta ttg cgc ttt ctc acg ctc acg ctg ccc           192
Thr Val Leu Leu Tyr Leu Leu Arg Phe Leu Thr Leu Thr Leu Pro
        50                  55                  60 cag gtg ctg ttc aat ttc tgc ggc ctg gta ttc tac aat gcc ttc ccc       240
Gln Val Leu Phe Asn Phe Cys Gly Leu Val Phe Tyr Asn Ala Phe Pro
65                  70                  75                  80 gag aag gtc gtc ctc aag ggc agc ccc ctg ctg gcg ccc ttc atc tgc       288
Glu Lys Val Val Leu Lys Gly Ser Pro Leu Leu Ala Pro Phe Ile Cys
                85                  90                  95 atc cgt gtg gtc acg cgc ggc gac ttc ccg gat ttg gtt aag acg aat       336
Ile Arg Val Val Thr Arg Gly Asp Phe Pro Asp Leu Val Lys Thr Asn
            100                 105                 110 gtg ctg cgc aac atg aac acc tgc cta gac acg gga ctg gag aac ttt       384
Val Leu Arg Asn Met Asn Thr Cys Leu Asp Thr Gly Leu Glu Asn Phe
        115                 120                 125 ctc atc gaa gtg gtc acg gac aag gcg gtg aat ctg tca cag cat cga       432
Leu Ile Glu Val Val Thr Asp Lys Ala Val Asn Leu Ser Gln His Arg
    130                 135                 140 cgc atc cga gag atc gtt gtg ccc aag gag tac aag acg aga acc ggg       480
Arg Ile Arg Glu Ile Val Val Pro Lys Glu Tyr Lys Thr Arg Thr Gly
145                 150                 155                 160 gcg ttg ttc aag tcg cgt gcc ctg cag tat tgc ctg gag gat aat gtg       528
Ala Leu Phe Lys Ser Arg Ala Leu Gln Tyr Cys Leu Glu Asp Asn Val
                165                 170                 175 aac gtg ctg aac gac agc gac tgg atc gtc cat ctg gat gag gag acg       576
Asn Val Leu Asn Asp Ser Asp Trp Ile Val His Leu Asp Glu Glu Thr
            180                 185                 190 ctg ctc acg gag aat tcg gtg cgt ggt atc att aac ttt gtg ctg gat       624
Leu Leu Thr Glu Asn Ser Val Arg Gly Ile Ile Asn Phe Val Leu Asp
        195                 200                 205 ggc aag cac ccg ttc ggc cag ggc ctg atc acc tat gcc aac gag aac       672
Gly Lys His Pro Phe Gly Gln Gly Leu Ile Thr Tyr Ala Asn Glu Asn
    210                 215                 220 gtg gtc aat tgg ctg acc aca ttg gcg gac agc ttt cgg gtc tcc gat       720
Val Val Asn Trp Leu Thr Thr Leu Ala Asp Ser Phe Arg Val Ser Asp
225                 230                 235                 240 gat atg ggc aag ctg cgt ctg cag ttc aag ctc ttt cac aag ccg ctc       768
Asp Met Gly Lys Leu Arg Leu Gln Phe Lys Leu Phe His Lys Pro Leu
                245                 250                 255 ttc agc tgg aag ggc agt tat gtg gtc acc cag gtg agt gct gag cgt       816
```

```
                                                  -continued

Phe Ser Trp Lys Gly Ser Tyr Val Val Thr Gln Val Ser Ala Glu Arg
            260                 265                 270 tca gtg tcc ttt gac aac gga atc gac ggt tcg gtg gcc gag gat tgc      864
Ser Val Ser Phe Asp Asn Gly Ile Asp Gly Ser Val Ala Glu Asp Cys
        275                 280                 285 ttc ttc gcg atg cgg gcc ttt agc cag ggc tac acg ttc aac ttc atc      912
Phe Phe Ala Met Arg Ala Phe Ser Gln Gly Tyr Thr Phe Asn Phe Ile
    290                 295                 300 gag ggc gaa atg tac gag aag tcg ccg ttc acg ctg ctg gac ttc ctg      960
Glu Gly Glu Met Tyr Glu Lys Ser Pro Phe Thr Leu Leu Asp Phe Leu
305                 310                 315                 320 cag cag agg aaa cga tgg ctc cag ggc att ctg ctg gtg gtc cac tcc     1008
Gln Gln Arg Lys Arg Trp Leu Gln Gly Ile Leu Leu Val Val His Ser
                325                 330                 335 aag atg atc ccg ttt aag cac aag ctc ctg ctg ggc atc agt gtc tat     1056
Lys Met Ile Pro Phe Lys His Lys Leu Leu Leu Gly Ile Ser Val Tyr
            340                 345                 350 tcg tgg gtc acc atg ccg ctg tcc acg tcg aac atc atc ttt gcg gca     1104
Ser Trp Val Thr Met Pro Leu Ser Thr Ser Asn Ile Ile Phe Ala Ala
        355                 360                 365 ctg tat ccc att ccc tgc cca aat ctg gtt gac ttt gtg tgc gcc ttc     1152
Leu Tyr Pro Ile Pro Cys Pro Asn Leu Val Asp Phe Val Cys Ala Phe
    370                 375                 380 atc gcg gcc att aat atc tac atg tac gtc ttt ggc gta atc aag tcc     1200
Ile Ala Ala Ile Asn Ile Tyr Met Tyr Val Phe Gly Val Ile Lys Ser
385                 390                 395                 400 ttt tca ctg tac cgc ttc ggt ttg ttc cga ttc ctg gcc tgc gtg ctg     1248
Phe Ser Leu Tyr Arg Phe Gly Leu Phe Arg Phe Leu Ala Cys Val Leu
                405                 410                 415 ggt gcg gtg tgc acg ata ccc gtg aat gtg gtt atc gag aat gtg gct     1296
Gly Ala Val Cys Thr Ile Pro Val Asn Val Val Ile Glu Asn Val Ala
            420                 425                 430 gtc att tgg ggc ctg gtg ggc aag aag cac aag ttc tat gtg gtt cag     1344
Val Ile Trp Gly Leu Val Gly Lys Lys His Lys Phe Tyr Val Val Gln
        435                 440                 445 aag gat gtg cgc gta ctg gag act gtc tag                             1374
Lys Asp Val Arg Val Leu Glu Thr Val
    450                 455

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcagatctc aagatgaact ccaccacaaa g                                    31

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatagtctag acagtctcca gtacgcg                                         27

<210> SEQ ID NO 6
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agcagatcta agattgacga gaactcgttc                                          30

<210> SEQ ID NO 7
<211> LENGTH: 458
<212> TYPE: PRT
<213> ORGANISM: Anopheles gambiae

<400> SEQUENCE: 7
```

Met Leu Asn Ser Thr Ser Lys His Ile Leu His Cys Ala Leu Leu Phe
 1               5                  10                  15

Gly Leu Leu Ile Val Phe Glu Ile Phe Cys Gly Gly Ile Lys Val Thr
            20                  25                  30

Glu Ser Ala Phe Val Ala Ile Asp Pro Trp Glu Glu Tyr Gly Thr Leu
        35                  40                  45

Leu Thr Ile Val Leu Tyr Leu Leu Arg Leu Leu Thr Phe Leu Thr Leu
    50                  55                  60

Pro Gln Val Leu Phe Asn Phe Gly Leu Val Ile Tyr Asn Ala Phe
65                  70                  75                  80

Pro Glu Lys Val Val Leu Lys Gly Ser Pro Leu Leu Ala Pro Phe Ile
                85                  90                  95

Cys Ile Arg Ile Val Thr Arg Gly Asp Tyr Ala Glu Leu Val Lys Thr
            100                 105                 110

Asn Val Leu Arg Asn Met Asn Thr Cys Leu Asp Thr Gly Leu Glu Asn
        115                 120                 125

Phe Leu Ile Glu Val Val Thr Asp Lys Pro Ile Gly Leu Pro Lys His
    130                 135                 140

Arg Arg Thr Arg Glu Ile Val Val Pro Lys Glu Tyr Lys Thr Lys Thr
145                 150                 155                 160

Gly Ala Met Phe Lys Ala Arg Ala Leu Gln Tyr Cys Leu Glu Asp Thr
                165                 170                 175

Val Asn Val Leu Asn Asn Asn Asp Trp Val Val His Leu Asp Glu Glu
            180                 185                 190

Thr Leu Leu Thr Glu Asn Ser Val Arg Gly Ile Ile Asn Phe Val Leu
        195                 200                 205

Asp Gly Lys His Pro Phe Gly Gln Gly Leu Ile Thr Tyr Ala Asn Glu
    210                 215                 220

Asn Val Val Asn Trp Leu Thr Thr Leu Ala Asp Ser Phe Arg Val Ser
225                 230                 235                 240

Asp Asp Met Gly Lys Leu Arg Leu Gln Phe Lys Met Phe His Lys Pro
                245                 250                 255

Tyr Phe Ser Trp Lys Gly Ser Tyr Val Val Thr Gln Val His Ala Glu
            260                 265                 270

Lys Ala Val Ser Phe Asp Asn Gly Ile Asp Gly Ser Val Ala Glu Asp
        275                 280                 285

Cys Phe Phe Ala Met Arg Ala Phe Ala Gln Gly Tyr Thr Phe Asn Phe
    290                 295                 300

Ile Glu Gly Glu Met Tyr Glu Lys Ser Pro Phe Thr Leu Thr Asp Phe
305                 310                 315                 320

```
Leu Gln Gln Arg Lys Arg Trp Leu Gln Gly Ile Leu Leu Val Val Arg
                325                 330                 335

Ser Thr Glu Ile Pro Leu Arg Asn Lys Val Leu Leu Gly Ile Ser Leu
                340                 345                 350

Cys Ser Trp Ile Thr Met Pro Leu Ser Thr Ser Asn Met Ile Phe Ala
                355                 360                 365

Ala Ile Tyr Pro Ile Pro Cys Pro Asn Leu Ile Asp Phe Val Cys Ala
                370                 375                 380

Phe Ile Ala Gly Phe Asn Ile Tyr Met Tyr Val Phe Gly Val Ile Lys
385                 390                 395                 400

Ser Phe Ser Leu Tyr Arg Phe Gly Leu Val Lys Phe Leu Ala Cys Val
                405                 410                 415

Leu Gly Ala Leu Cys Thr Ile Pro Ile Asn Val Val Ile Glu Asn Val
                420                 425                 430

Ala Val Ile Trp Gly Leu Val Gly Lys Lys Asn Lys Phe Tyr Val Val
                435                 440                 445

Gln Lys Asp Val Arg Ala Leu Val Thr Val
                450                 455

<210> SEQ ID NO 8
<211> LENGTH: 455
<212> TYPE: PRT
<213> ORGANISM: Caenorhabditis elegans

<400> SEQUENCE: 8

Met Asn Cys Glu Val Lys His Ala Leu His Cys Ala Val Leu Val Ala
1               5                   10                  15

Trp Ile Val Cys Phe Ala Tyr Phe Cys Gly Val Phe Thr Glu Pro Val
                20                  25                  30

Glu Gly Ser Val Pro Glu Ser Pro Val Ala Ser Tyr Gly Leu Ile Trp
                35                  40                  45

Thr Val Cys Leu Tyr Leu Leu Arg Phe Thr Ala Leu Leu Val Leu Pro
            50                  55                  60

Gln Cys Leu Cys Asn Leu Gly Gly Leu Met Met Phe Asn Ala Phe Arg
65                  70                  75                  80

Glu Lys Val Gln Leu Lys Ala Ala Pro Leu Leu Ser Pro Phe Val Cys
                85                  90                  95

Phe Arg Val Val Thr Lys Gly Asn Phe Pro Leu Leu Val Lys Glu Asn
                100                 105                 110

Ile Asp Thr Asn Met Lys Thr Cys Phe Glu Ala Gly Met Glu Asn Phe
            115                 120                 125

Ile Phe Glu Val Val Thr Asp Lys Ala Ile Asn Leu Pro Pro Asn Pro
130                 135                 140

Arg Val Arg Glu Val Val Val Pro Thr Val Tyr Lys Thr Lys Ser Gly
145                 150                 155                 160

Ala Lys Phe Lys Ala Arg Ala Leu Gln Tyr Cys Leu Glu Asp Asp Val
                165                 170                 175

Asn Ile Leu Gln Pro Thr Asp Trp Ile Val His Leu Asp Glu Glu Thr
            180                 185                 190

Leu Leu Thr Thr Asn Ala Ile Cys Gly Ile Leu Asn Phe Cys Glu Asp
                195                 200                 205

Gly Lys His Gln Phe Gly Gln Gly Val Ile Thr Tyr Ala Asn Gly Asp
        210                 215                 220

Ile Val Asn Trp Leu Thr Thr Leu Ser Asp Ser Phe Arg Val Ala Asp
225                 230                 235                 240
```

-continued

```
Asp Met Gly Lys Leu Arg Phe Gln Phe Lys Leu Phe His Lys Pro Leu
            245                 250                 255

Phe Gly Trp Lys Gly Ser Tyr Val Val Thr Gln Val Glu Ala Glu Arg
            260                 265                 270

Asp Val Ser Tyr Asp His Gly Met Glu Gly Ser Ile Ala Glu Asp Cys
            275                 280                 285

Phe Phe Ser Met Val Ala Met Lys His Gly Tyr Ser Phe Asp Phe Ile
        290                 295                 300

Glu Gly Glu Met His Glu Lys Ser Pro Phe Thr Met Trp Asp Phe Leu
305                 310                 315                 320

Gln Gln Arg Lys Arg Trp Leu Gln Gly Ile Leu Leu Thr Val His Ser
            325                 330                 335

Ser Lys Ile Ala Val Val His Lys Ala Leu Leu Ala Leu Ser Leu Tyr
            340                 345                 350

Ala Trp Ala Thr Met Pro Leu Thr Ser Leu Gln Val Phe Leu Cys Pro
            355                 360                 365

Leu Phe Pro Leu Pro Arg Cys Leu Pro Phe Asp Phe Leu Leu Ser Phe
        370                 375                 380

Val Gly Ala Leu Asn Leu Tyr Met Tyr Ile Phe Gly Val Val Lys Ser
385                 390                 395                 400

Phe Ser His Lys Tyr Arg Asn Ser Leu Leu Arg Leu Ala Met Tyr Leu
            405                 410                 415

Ala Gly Ala Leu Met Thr Ile Pro Phe Asn Ile Leu Ile Glu Asn Ala
            420                 425                 430

Ala Val Leu Val Gly Met Phe Gly Arg Lys Asp Gln Phe Tyr Ile Val
            435                 440                 445

Asn Lys Asp Ile Gln Thr Val
450                 455
```